United States Patent
Bhat et al.

(10) Patent No.: US 12,318,430 B2
(45) Date of Patent: *Jun. 3, 2025

(54) METHODS OF TREATING NEUTORPENIA USING G-CSF PROTEIN COMPLEX

(71) Applicants: Spectrum Pharmaceuticals Inc., Lake Forest, IL (US); Hanmi Pharm Co., Ltd., Gyeonggi-do (KR)

(72) Inventors: Gajanan Bhat, Lake Forest, IL (US); Shanta Chawla, Lake Forest, IL (US); Jae Hyuk Choi, Gyeonggi-do (KR); Eun Jung Kim, Gyeonggi-do (KR); Yu Yon Kim, Gyeonggi-do (KR); Gyu Hyan Lee, Gyeonggi-do (KR); Hyesun Han, Gyeonggi-do (KR)

(73) Assignees: SPECTRUM PHARMACEUTICALS, INC., Lake Forest, IL (US); HANMI PHARM CO., LTD., Gyeonggi-do (KR)

( * ) Notice: Subject to any disclaimer, the term of this patent is extended or adjusted under 35 U.S.C. 154(b) by 36 days.

This patent is subject to a terminal disclaimer.

(21) Appl. No.: 18/181,852

(22) Filed: Mar. 10, 2023

(65) Prior Publication Data

US 2023/0270822 A1     Aug. 31, 2023

Related U.S. Application Data

(63) Continuation of application No. 16/996,635, filed on Aug. 18, 2020, now Pat. No. 11,684,655, which is a continuation-in-part of application No. 16/428,351, filed on May 31, 2019, now Pat. No. 11,267,858.

(51) Int. Cl.
| | | |
|---|---|---|
| *A61K 38/19* | (2006.01) | |
| *A61K 47/60* | (2017.01) | |
| *C07K 16/46* | (2006.01) | |

(52) U.S. Cl.
CPC ............ *A61K 38/193* (2013.01); *A61K 47/60* (2017.08); *C07K 16/46* (2013.01); *C07K 2317/522* (2013.01); *C07K 2317/524* (2013.01); *C07K 2317/526* (2013.01); *C07K 2317/528* (2013.01); *C07K 2317/53* (2013.01)

(58) Field of Classification Search
CPC ...... A61K 38/193; A61K 47/60; C07K 16/46; C07K 2317/53
See application file for complete search history.

(56) References Cited

U.S. PATENT DOCUMENTS

| | | | | |
|---|---|---|---|---|
| 9,421,244 | B2 * | 8/2016 | Kim | A61P 35/00 |
| 2010/0227818 | A1 * | 9/2010 | Bock | A61P 43/00 |
| | | | | 424/85.1 |
| 2012/0294829 | A1 * | 11/2012 | Lee | A61K 38/193 |
| | | | | 424/85.1 |

FOREIGN PATENT DOCUMENTS

| | | | | |
|---|---|---|---|---|
| WO | WO-0228896 A1 * | 4/2002 | ........... | C07K 14/535 |
| WO | WO-2014193173 A1 * | 12/2014 | ........... | A61K 38/193 |
| WO | WO-2018144764 A1 * | 8/2018 | ........... | A61K 31/337 |

OTHER PUBLICATIONS

Lakhanpal et al. (Breast Cancer Manage. 2(5) 367-374, 2013).*
U.S. Appl. No. 18/318,492; Non-Final Office Action, dated Sep. 5, 2024; 37 pages.

* cited by examiner

*Primary Examiner* — Gyan Chandra
(74) *Attorney, Agent, or Firm* — Weaver Austin Villeneuve & Sampson LLP

(57) ABSTRACT

This disclosure provides a method of preventing, alleviating or treating a condition (i.e., neutropenia) in a subject in need thereof, the condition characterized by compromised white blood cell production in the subject. The method includes administering to the subject a therapeutically effective amount of a protein complex on the same day as a chemotherapy regimen, wherein the protein complex is a modified human granulocyte-colony stimulating factor (hG-CSF) covalently linked to an immunoglobulin Fc region via a non-peptidyl polymer. The non-peptidyl polymer is site-specifically linked to an N-terminus of the immunoglobulin Fc region, and the modified hG-CSF comprises substitutions in at least one of Cys17 and Pro65.

15 Claims, 6 Drawing Sheets
Specification includes a Sequence Listing.

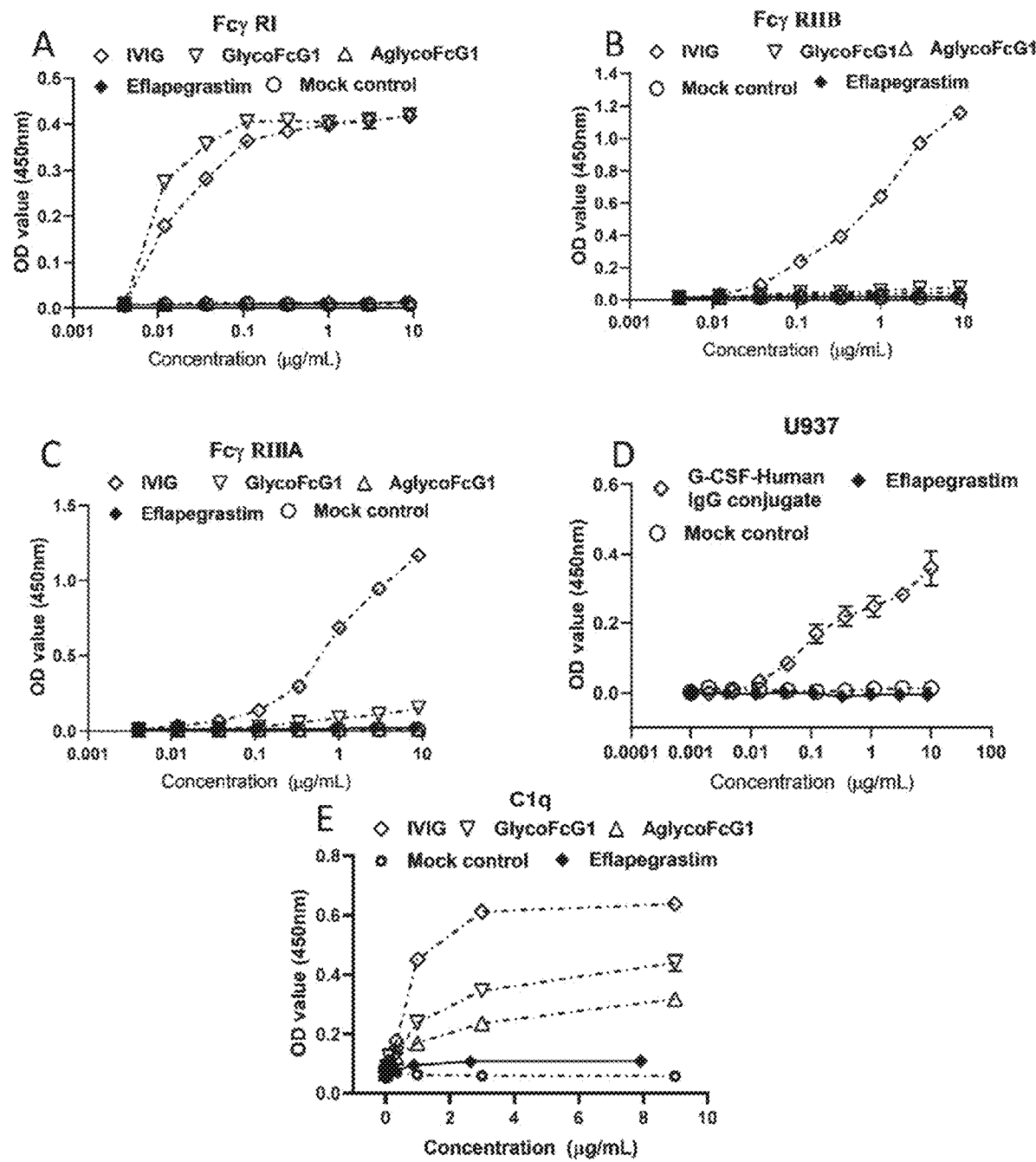
FIGS. 4A, 4B, 4C, 4D, and 4E

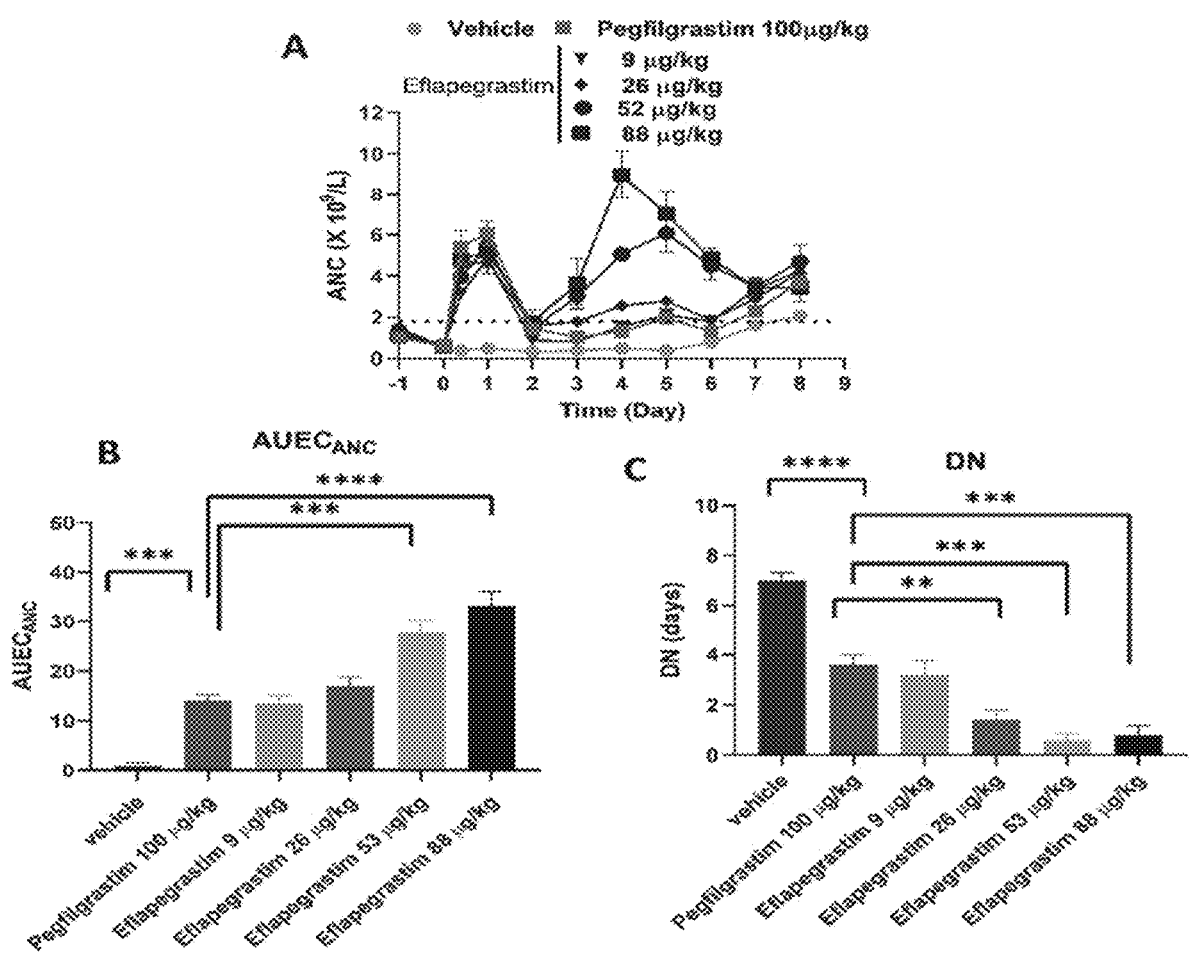
FIGS. 6A, 6B, and 6C

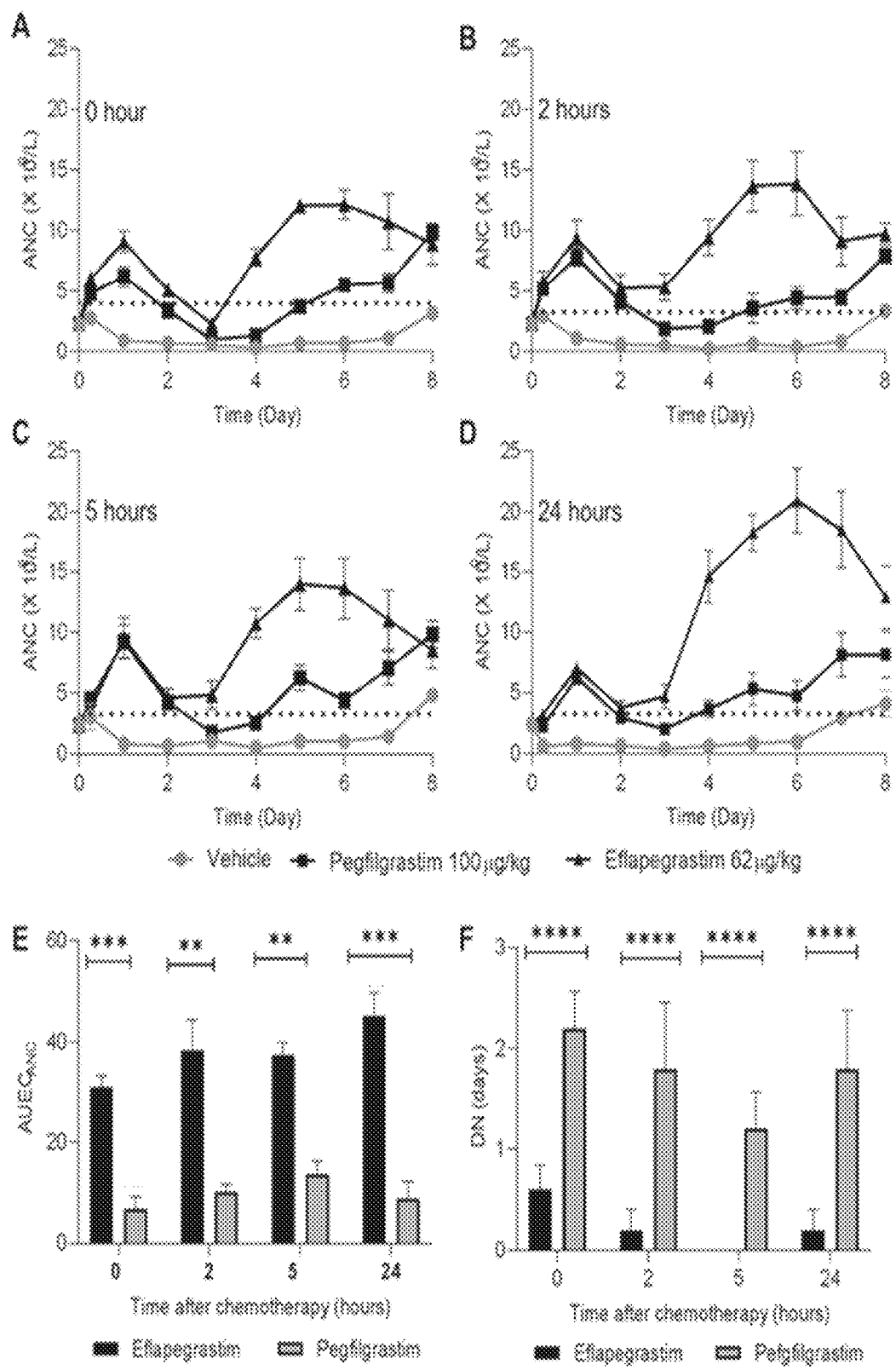
FIGS. 7A, 7B, 7C, 7D, 7E, and 7F

METHODS OF TREATING NEUTORPENIA USING G-CSF PROTEIN COMPLEX

CROSS-REFERENCE TO RELATED APPLICATIONS

The present application is a continuation of U.S. Nonprovisional patent application Ser. No. 16/996,635, filed Aug. 18, 2020, which is a continuation-in-part of U.S. Nonprovisional patent application Ser. No. 16/428,351, filed May 31, 2019, now U.S. Pat. No. 11,267,858. The foregoing applications are incorporated by reference herein in their entireties.

SEQUENCE LISTING

The sequence listing of the present application is submitted electronically as ST.26 formatted sequence listing with a file name "178923.00396.xml," a creation date of Mar. 10, 2023, and a size of 2,971 bytes. This sequence listing submitted is part of the specification and is hereby incorporated by reference in its entirety.

TECHNICAL FIELD

The present invention relates to protein complexes, pharmaceutical compositions, and methods of use thereof for treating, preventing, or reducing the risk of developing a condition, such as neutropenia. The protein complex can be formed by linking an immunoglobulin Fc region to a physiologically active polypeptide via a non-peptidyl polymer, in which the non-peptidyl polymer is linked to the immunoglobulin Fc region.

BACKGROUND OF THE INVENTION

Neutropenia is a relatively common disorder most often due to chemotherapy treatments, adverse drug reactions, or autoimmune disorders. Chemotherapy-induced neutropenia is a common toxicity caused by the administration of anticancer drugs. It is associated with life-threatening infections and may alter the chemotherapy schedule, thus impacting on early and long-term outcome. Febrile Neutropenia (FN) is a major dose-limiting toxicity of myelosuppressive chemotherapy regimens such as docetaxel, doxorubicin, cyclophosphamide (TAC); dose-dense doxorubicin plus cyclophosphamide (AC), with or without subsequent weekly or semiweekly paclitaxel; and docetaxel plus cyclophosphamide (TC). It usually leads to prolonged hospitalization, intravenous administration of broad-spectrum antibiotics, and is often associated with significant morbidity and mortality. About 25% to 40% of treatment naïve patients develop febrile neutropenia with common chemotherapy regimens.

Current therapeutic modalities employ granulocyte colony-stimulating factor (G-CSF) and/or antibiotic agents to combat this condition. G-CSF or its other polypeptide derivatives are easy to denature or easily de-composed by proteolytic enzymes in blood to be readily removed through the kidney or liver. Therefore, to maintain the blood concentration and titer of the G-CSF containing drugs, it is necessary to frequently administer the protein drug to patients, which causes excessive suffering in patients. To solve such problems, G-CSF was chemically attached to polymers having a high solubility such as polyethylene glycol ("PEG"), thereby increasing its blood stability and maintaining suitable blood concentration for a longer time.

Filgrastim, tbo-filgrastim, and pegfilgrastim are G-CSFs currently approved by the US Food and Drug Administration (FDA) for the prevention of chemotherapy-induced neutropenia, While the European guidelines also include lenograstim as a recommended G-CSF in solid tumors and non-myeloid malignancies, it is not approved for use in the US. Binding of PEG to G-CSF, even though may increase blood stability, does dramatically reduce the titer needed for optimal physiologic effect. Thus there is a need to address this shortcoming in the art.

The present invention provides new formulations and methods of use where the new G-CSF containing protein complex can stay stable and dramatically improve patient outcomes.

SUMMARY OF THE INVENTION

The present invention is directed to methods of using a G-CSF containing a more stable protein complex that can be easily prepared and administered to patients at risk of developing neutropenia, and maintain a serum concentration that achieves the optimal therapeutic outcome. Another aspect of the present invention is directed to a protein complex prepared by linking a physiologically active polypeptide and an immunoglobulin Fc fragment via a non-peptidyl polymer, in which the non-peptidyl polymer is site-specifically linked to an N-terminus of the immunoglobulin Fc fragment. In at least some embodiment, the protein compels is administered on the same day as the chemotherapeutic agent.

In another aspect, the present invention provides a method of preparing the protein complex in a pharmaceutical composition for improving in vivo duration and stability of the physiologically active polypeptide, the composition including the protein complex as an active ingredient.

In yet another aspect, the present invention provides methods for preventing, alleviating, or treating a condition in a subject in need thereof. The condition is characterized by compromised white blood cell production in the subject. The method comprises administering to the subject a therapeutically effective amount of a protein conjugate comprising a modified human granulocyte-colony stimulating factor (hG-CSF) covalently linked to an immunoglobulin Fc region via a non-peptidyl polymer, wherein the non-peptidyl polymer is site-specifically linked to an N-terminus of the immunoglobulin Fc region, and the modified hG-CSF comprises substitutions in at least one of Cys17 and Pro65. In at least some embodiment, the protein compels is administered on the same day as the chemotherapeutic agent.

In another aspect, the present invention is directed to a method for treating or preventing neutropenia in a patient diagnosed with breast cancer comprising administering a chemotherapy regimen of docetaxol and cyclophosphamide and a protein complex comprising a physiologically active polypeptide linked to an immunoglobulin Fc region via a non-peptidyl polymer, wherein the non-peptidyl polymer is site-specifically linked to a N-terminus of the immunoglobulin Fc region, and wherein both ends of the non-peptidyl polymer is respectively linked to the physiologically active polypeptide and the immunoglobulin Fc region through reactive groups by a covalent bond. In at least some embodiment, the protein compels is administered on the same day as the chemotherapeutic agent.

In another embodiment, the present invention provides methods of preventing, alleviating or treating FN in patients suffering or at risk of developing breast cancer, who were previously treated with a myelosuppressive or chemotherapeutic drug regimen agents with G-CSF to mitigate the potential neutropenia that results from the administration of such drug regimen. In yet another embodiment, the G-CSF will be administered approximately 24 hours after the drug regimen. In another embodiment, the G-CSF will be administered product as the same day as the drug regimen, preferably 30 minutes, 1, hour, 3 hours, 5 hours, 6, hours, 7 hours, 8 hours, 12 or 24 hours after administration of the last drug of the regimen.

BRIEF DESCRIPTION OF THE DRAWINGS

FIGS. 4A, 4B, 4C, 4D, and 4E (collectively "FIG. 4") are a set of graphs showing binding of eflapegrastim to Fcγ receptors and C1q. Binding of eflapegrastim to purified Fcγ receptors Fcγ RI (FIG. 4A), Fcγ RIIB (FIG. 4B), and Fcγ RIIIA (FIG. 4C), and Fcγ receptors on U937 cells FIG. 4 (FIG. 4D) and C1q (FIG. 4E) was studied by ELISA. The concentration of individual test articles was calculated based on the theoretical Fc protein to make equivalent molarity. Mean OD values from duplicate samples are presented. The error bars represent SEM values. OD: Optical density; IVIG: intravenous immunoglobulin G (immunoglobulin G); GlycoFcG1: glycosylated Fc fragment of human IgG1; AglycoFcG1: Aglycosylated Fc fragment of human IgG1.

FIGS. 6A, 6B, and 6C (collectively "FIG. 6") are a set of graphs showing efficacy in neutropenic rats following administration of eflapegrastim and pegfilgrastim 24 hours after CPA chemotherapy. Rats were administered with cyclophosphamide (50 mg/kg) to induce neutropenia and treated with eflapegrastim or pegfilgrastim 24 hours later. Blood samples were collected from jugular vein, and ANC was determined using hematology analyzer. FIG. 6A shows the ANC profile. FIG. 6B shows area under the ANC versus. Time curve above baseline (AUEC$_{ANC}$). FIG. 6C shows the duration of neutropenia (DN), determined by computing the number of days ANC was below the ANC of untreated control group during the recovery period. The data are mean values from 5 animals. The error bars represent SEM values. $p<0.01$; *$p<0.001$; ****$p<0.0001$.

FIGS. 7A, 7B, 7C, 7D, 7E, and 7F (collectively "FIG. 7") are a set of graphs showing efficacy in neutropenic rats following administration of eflapegrastim and pegfilgrastim concomitantly and at different times up to 24 hours after docetaxel-CPA (TC) chemotherapy. Rats were administered with docetaxel (4 mg/kg) and CPA (32 mg/kg) to induce neutropenia and treated with eflapegrastim or pegfilgrastim at 0, 2, 5, and 24 hours after chemotherapy. Blood samples were collected via jugular vein up to 8 days. FIGS. 7A, 7B, 7C, and 7D show ANC profiles following administration of eflapegrastim or pegfilgrastim at 0, 2, 5, and 24 hours after chemotherapy, respectively. FIG. 7E shows area under the ANC versus. Time curve above baseline (AUEC$_{ANC}$). FIG. 7F shows the duration of neutropenia (DN), determined by computing the number of days ANC was below the ANC of untreated control group during the recovery period. The data are mean values from 5 animals. The error bars represent SEM values. $p<0.01$; *$p<0.001$; ****$p<0.0001$

DETAILED DESCRIPTION OF THE INVENTION

Figure 1A:
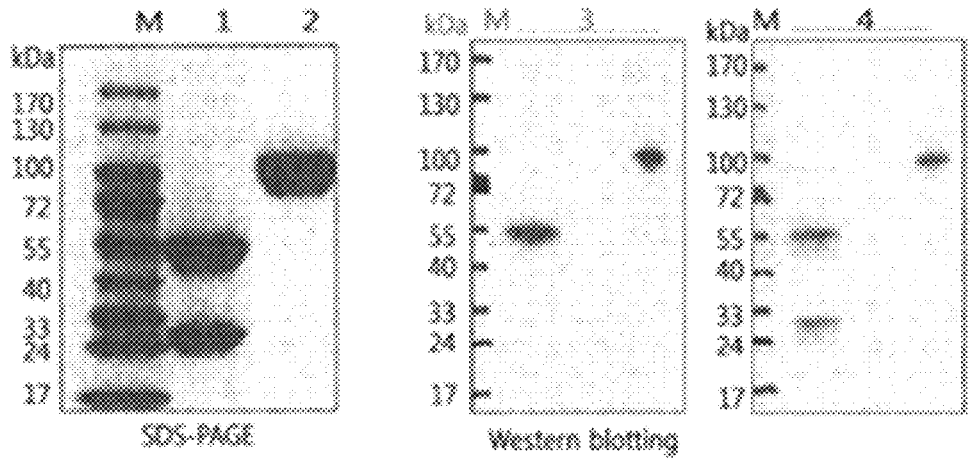
FIG. 1A shows results of SDS-PAGE and western blotting of a $^{17,65}$Ser-G-CSF-PEG-Fc complex, which was prepared by N-terminal reaction of an immunoglobulin Fc region.

Broadly speaking, the present invention is directed to methods of preventing, alleviating, prophylactically treating, and treating a subject patient having a condition characterized by compromised white blood cell production. The method includes administering to the subject a therapeutically effective amount of a protein complex comprising a modified human granulocyte-colony stimulating factor (hG-CSF) covalently linked to an immunoglobulin Fc region via a non-peptidyl polymer, wherein the non-peptidyl polymer is site-specifically linked to an N-terminus of the immunoglobulin Fc region, and the modified hG-CSF comprises substitutions in at least one of Cys17 and Pro65. In at least some embodiment, the protein compels is administered on the same day as the chemotherapeutic agent.

In another aspect, the present invention is directed to a method for increasing the number of granulocytes in eligible patients for a bone marrow transplant. The method includes administering to the subject a therapeutically effective amount of a protein complex comprising a modified human granulocyte-colony stimulating factor (hG-CSF) covalently linked to an immunoglobulin Fc region via a non-peptidyl polymer, wherein the non-peptidyl polymer is site-specifically linked to an N-terminus of the immunoglobulin Fc region, and the modified hG-CSF comprises substitutions in at least one of Cys17 and Pro65. In at least some embodiment, the protein compels is administered on the same day as the chemotherapeutic agent.

In yet another aspect, the present invention is directed to a method for increasing stem cell production in a subject. The method includes administering to the subject a therapeutically effective amount of a protein complex comprising a modified human granulocyte-colony stimulating factor (hG-CSF) covalently linked to an immunoglobulin Fc region via a non-peptidyl polymer, wherein the non-peptidyl polymer is site-specifically linked to an N-terminus of the immunoglobulin Fc region, and the modified hG-CSF comprises substitutions in at least one of Cys17 and Pro65. In at least some embodiment, the protein compels is administered on the same day as the chemotherapeutic agent.

In yet another aspect, the present invention is directed to increasing the number of hematopoietic progenitor cells in a patient undergoing chemotherapy or in a patient who is a donor of a stem cell donor to a patient. The method includes administering to the subject a therapeutically effective amount of a protein conjugate comprising a modified human granulocyte-colony stimulating factor (hG-CSF) covalently linked to an immunoglobulin Fc region via a non-peptidyl polymer, wherein the non-peptidyl polymer is site-specifically linked to an N-terminus of the immunoglobulin Fc region, and the modified hG-CSF comprises substitutions in at least one of Cys17 and Pro65. In at least some embodiment, the protein compels is administered on the same day as the chemotherapeutic agent.

In yet another embodiment, the present invention is directed to a method for increasing stem cell production in a donor, comprising administering to the subject a therapeutically effective amount of a protein conjugate comprising administering to the subject a therapeutically effective amount of a chemotherapeutic regimen followed by a therapeutically effective amount of a protein complex comprising a modified human granulocyte-colony stimulating factor (hG-CSF) covalently linked to an immunoglobulin Fc region via a non-peptidyl polymer, wherein the non-peptidyl polymer is site-specifically linked to an N-terminus of the immunoglobulin Fc region and the modified hG-CSF comprises substitutions in at least one of Cys17 and Pro65, wherein the protein complex is administered on the same day as the chemotherapeutic regimen.

In certain aspect, the conditions to be treated include reduced hematopoietic function, reduced immune function, reduced neutrophil count, reduced neutrophil mobilization, mobilization of peripheral blood progenitor cells, sepsis, severe chronic neutropenia, bone marrow transplants, infectious diseases, leucopenia, thrombocytopenia, anemia, enhancing engraftment of bone marrow during transplantation, enhancing bone marrow recovery in treatment of radiation, chemical or chemotherapeutic induced bone marrow aplasia or myelosuppression, and acquired immune deficiency syndrome. In one embodiment, the condition is myelosuppression, neutropenia, or preferably febrile neutropenia.

In another aspect, the present invention is directed to a method for preventing, alleviating, prophylactically treating, and treating an infection as manifested by neutropenia (e.g., febrile neutropenia in the subject with non-myeloid malignancies receiving myelosuppressive anti-cancer drugs. The method includes administering to the subject a therapeutically effective amount of a protein complex comprising a modified human granulocyte-colony stimulating factor (hG-CSF) covalently linked to an immunoglobulin Fc region via a non-peptidyl polymer, wherein the non-peptidyl polymer is site-specifically linked to an N-terminus of the immunoglobulin Fc region, and the modified hG-CSF comprises substitutions in at least one of Cys17 and Pro65.

In some embodiments, the compromised white blood cell production is a result of chemotherapy, radiation therapy, adjuvant or neoadjuvant chemotherapy, or idiopathic thrombocytopenic purpura. In certain embodiments, the adjuvant or neoadjuvant chemotherapy is a combination of docetaxel and cyclophosphamide.

In some embodiments, the therapeutically effective amount is a unit dosage between about 5 µg/kg and about 200 µg/kg. In some embodiments, the therapeutically effective amount is a unit dosage form selected from: about 9 µg/kg, about 25 µg/kg, about 26 µg/kg, about 50 µg/kg, about 52 µg/kg, about 100 µg/kg, about 88 µg/kg, and about 200 µg/kg.

In certain embodiments, the present methodology further includes administering to the subject a therapeutically effective amount of a second agent, such as an anti-cancer agent. In certain embodiments, the modified G-CSF is by way of a substitution at Cys17 is Cys17Ser. In other embodiments, the substitution at Pro65 is Pro65Ser. In certain embodiments, the substitution is both the substitution Cys17Ser and Pro65Ser may be referred herein as $Ser^{17,65}$.

In some embodiments, the immunoglobulin Fc region comprises a polypeptide sequence of SEQ ID NO: 1. In some embodiments, the modified G-CSF comprises a polypeptide sequence of SEQ ID NO: 2.

| SEQ ID NO | SEQUENCE | OTHER INFORMATION |
|---|---|---|
| SEQ ID NO: 1 | TPLGPASSLPQSFLLKSLEQVRKIQGDGAALQEK LCATYKLCHPEELVLLGHSLGIPWAPLSSCSSQA LQLAGCLSQLHSGLFLYQGLLQALEGISPELGPT LDTLQLDVADFATTIWQQMEELGMAPALQPTQGA MPAFASAFQRRAGGVLVASHLQSFLEVSYRVLRH LAQP | G-CSF (17Ser and 65Ser) |
| SEQ ID NO: 2 | PSCPAPEFLGGPSVFLFPPKPKDTLMISRTPEVT CVVVDVSQEDPEVQFNWYVDGVEVHNAKTKPREE QFNSTYRVVSVLTVLHQDWLNGKEYKCKVSNKGL PSSIEKTISKAKGQPREPQVYTLPPSQEEMTKNQ VSLTCLVKGFYPSDIAVEWESNGQPENNYKTTPP VLDSDGSFFLYSRLTVDKSRWQEGNVFSCSVMHE ALHNHYTQKSLSLSLGK | Immunoglobulin Fc region (IgG4) |

In some embodiments, the protein complex employed in the present methods contain (a) each domain of the immunoglobulin Fc fragment is a hybrid of domains, in which each domain has a different origin derived from immunoglobulins selected from the group consisting of IgG, IgA, IgD, IgE, and IgM; (b) the immunoglobulin Fc fragment is a dimer or multimer consisting of single-chain immunoglobulins comprising domains having the same origin; (c) the immunoglobulin Fc fragment is an IgG4 Fc fragment; or (d) the immunoglobulin Fc fragment is a human aglycosylated IgG4 Fc fragment.

In certain embodiments, the non-peptidyl polymer is selected from the group consisting of polyethylene glycol, polypropylene glycol, an ethylene glycol-propylene glycol copolymer, polyoxyethylated polyol, polyvinyl alcohol, polysaccharide, dextran, polyvinyl ethyl ether, a biodegradable polymer, a lipid polymer, chitin, hyaluronic acid, and a combination thereof. In a preferred embodiment, the non-peptidyl polymer is polyethylene glycol.

Another aspect of the present invention is directed to methods for treating or preventing neutropenia in a patient receiving chemotherapy comprising administering to said patient a protein complex comprising a modified G-CSF linked to an immunoglobulin Fc region via a non-peptidyl polymer, wherein the non-peptidyl polymer is site-specifically linked to an N-terminus of the immunoglobulin Fc region. In some embodiments, both ends of the non-peptidyl polymer are respectively linked to the physiologically active polypeptide and the immunoglobulin Fc region through reactive groups by a covalent bond. In a preferred embodiment, the immunoglobulin Fc region is aglycosylated. In at least some embodiment, the protein compels is administered on the same day as the chemotherapeutic agent.

In some embodiments, the G-CSF complex composition is administered to the patient within about 26, 24, 18, 12, 8, 6, 5, 3, 2, 1, or half-hour of the completion of chemotherapy. In some embodiments, the G-CSF complex is administered concurrently with the chemotherapy.

In certain embodiments, the G-CSF complex is a $Ser^{17, 65}$-GCSF-polyethylene glycol-IgG4-Fc, which is the conjugate of a recombinant human GCSF analog and human IgG4-Fc fragment connected via two chemical bonds between an amino group of N-terminus in each protein and one molecule of polyethylene glycol dialdehyde. In some embodiment, the G-CSF complex is a $^{17,65S}$G-CSF-PEG-Fc protein complex.

In some embodiments, the present invention is directed to a method for treating or preventing neutropenia in a patient diagnosed with a cancer selected from the group consisting of non-small cell lung cancer, breast cancer, gastric cancer, colon cancer, pancreatic cancer, prostate cancer, myeloma, head and neck cancer, ovarian cancer, esophageal cancer, and metastatic cell carcinoma, comprising administering a chemotherapy regimen and a protein complex at the same day wherein the protein complex is administered within about 26, 24, 22, 18, 12, 8, 6, 5, 3, 2, 1, or half hour of the completion of chemotherapy.

In certain embodiments, the present invention is directed to a method for treating or preventing neutropenia in a patient diagnosed with breast cancer comprising administering a chemotherapy regimen of docetaxel and cyclophosphamide and therapeutically effective amounts of $^{17,65S}$G-CSF-PEG-Fc protein complex at doses of about 13.2 mg/0.6 mL (3.6 mg G-CSF equivalent), wherein the protein complex is administered 30 minutes, 2 hours, 3 hours, 5 hours, 8 hours, or 12 hours from the end of docetaxol and cyclophosphamide administration. In some embodiments, the chemotherapy regimen consisted of 3, 4, 5 or 6 cycles of 21 days, wherein on Day 1 of each cycle: (i) Docetaxel was administered at 75 mg/m² IV infusion per institute's standard of care (ii) Cyclophosphamide 600 mg/m² IV infusion.

In certain embodiment, duration of neutropenia from the first occurrence of an ANC below the threshold is unexpectedly superior for $^{17,65S}$G-CSF-PEG-Fc protein complex (eflapegrastim) in patients suffering from non-small cell lung cancer, breast cancer, gastric cancer, colon cancer, pancreatic cancer, prostate cancer, myeloma, head and neck cancer, ovarian cancer, esophageal cancer and metastatic cell carcinoma, as compared to other G-CSF or analogs thereof. In some embodiment, such superior results may be observed in any of the treatment cycles including but not limited to cycle 1, 2, 3 or 4. In certain embodiments, the incidences of adverse events were substantially lower as measured by competent clinical assessments as compared to other G-CSF or analogs thereof. In certain embodiments, the patient is diagnosed with breast cancer. In other embodiments, the duration of neutropenia is assessed based on the severity as the number of postdose days of severe neutropenia (ANC<0.5×10⁹/L) from the first occurrence of an ANC below the threshold.

In certain embodiment, duration of neutropenia is unexpectedly superior for $^{17,65S}$G-CSF-PEG-Fc protein complex (eflapegrastim) as compared to other G-CSF or analogs thereof in patients suffering from breast cancer, when at least one dose of $^{17,65S}$G-CSF-PEG-Fc protein complex is administered about 26, 24, 18, 12, 8, 6, 5, 3, 2, 1, or half-hour of the completion of chemotherapy. In certain embodiments, $^{65S}$G-CSF-PEG-Fc protein complex is administered about 6, 5, 3, 2, 1, or half hour of the completion of chemotherapy. In some embodiment, the chemotherapy comprises therapeutically effective doses of docetaxol and cyclophosphamide. In some embodiments, such superior results may be observed in any of the treatment cycles including but not limited to cycle 1, 2, 3 or 4. In certain embodiments, the incidences of adverse events were substantially lower as measured by competent clinical assessments as compared to other G-CSF or analogs thereof.

In some embodiments, the present invention provides the protein complex in which the immunoglobulin Fc region consists of one to four domains selected from the group consisting of CH1, CH2, CH3, and CH4 domains. In yet another embodiment, the present invention provides the protein complex in which the immunoglobulin Fc region further includes a hinge region.

In some embodiments, the present invention provides the protein complex in which the immunoglobulin Fc region is an immunoglobulin Fc fragment derived from IgG, IgA, IgD, IgE, or IgM. In yet another embodiment, the present invention provides the protein complex in which each domain of the immunoglobulin Fc fragment is a hybrid of domains and each domain has a different origin derived from immunoglobulins selected from the group consisting of IgG, IgA, IgD, IgE, and IgM. Still another specific embodiment of the present invention is directed to the use of the protein complex in which the immunoglobulin Fc fragment is a dimer or multimer consisting of single chain immunoglobulins comprising domains having the same origin. In another specific embodiment of the present invention provides the protein complex in which the immunoglobulin Fc fragment is an IgG4 Fc fragment.

In some embodiments, the present invention provides the protein complex in which the non-peptidyl polymer is selected from the group consisting of polyethylene glycol, polypropylene glycol, an ethylene glycol-propylene glycol copolymer, polyoxyethylated polyol, polyvinyl alcohol, polysaccharide, dextran, polyvinyl ethyl ether, a biodegradable polymer, a lipid polymer, chitin, hyaluronic acid, and a combination thereof, preferably the non-peptidyl polymer is polyethylene glycol. In some embodiments, the non-peptidyl polymer is 3.4 kDa polyethylene glycol.

In some embodiments, the present invention provides the protein complex in which the reactive group of the non-peptidyl polymer is selected from the group consisting of an aldehyde group, a maleimide group, and a succinimide derivative.

In some embodiments, the present invention provides the protein complex in which the aldehyde group is a propionaldehyde group or a butyraldehyde group.

In some embodiments, the present invention provides the protein complex in which the succinimide derivative is succinimidyl carboxymethyl, succinimidyl valerate, succinimidyl methylbutanoate, succinimidyl methylpropionate, succinimidyl butanoate, succinimidyl propionate, N-hydroxysuccinimide, or succinimidyl carbonate.

In some embodiments, the present invention provides the protein complex in which the non-peptidyl polymer has an aldehyde group as a reactive group at both ends.

In some embodiments, the present invention provides the protein complex in which the non-peptidyl polymer has an aldehyde group and a maleimide group as a reactive group at both ends, respectively.

In some embodiments, the present invention provides the protein complex in which the non-peptidyl polymer has an aldehyde group and a succinimide group as a reactive group at both ends, respectively.

In some embodiments, the present invention provides the protein complex in which each end of the non-peptidyl polymer is linked to the N-terminus of the immunoglobulin Fc region; and the N-terminus, C-terminus, or a free reactive group of a lysine residue, a histidine residue, or a cysteine residue of the physiologically active polypeptide, respectively.

In some embodiments, the present invention provides the protein complex in which the physiologically active polypeptide is selected from the group consisting of a hormone, a cytokine, an enzyme, an antibody, a growth factor, a transcription factor, a blood coagulation factor, a vaccine, a structural protein, a ligand protein, and a receptor.

In certain embodiments, the protein complex is a Ser$^{17}$, $^{65}$-GCSF-polyethylene glycol-IgG4-Fc which is the conjugate of a recombinant human GCSF analog and human IgG4-Fc fragment connected via two chemical bonds between an amino group of N-terminus in each protein and one molecule of polyethylene glycol dialdehyde with the molecular weight ranging from 1 kDa to 200 kDa, preferably between 1 kDa to 100 kDa. In one embodiment, the molecular weight of the protein complex, including the GCSF analog, the IgG4-FC fragment, and the polyethylene glycol dialdehyde is 72 kDa.

In another aspect, the present invention provides a method of preparing the protein complex, the method comprising:
(a) preparing a protein complex by linking at least one non-peptidyl polymer having a reactive group at both ends, at least one physiologically active polypeptide, and at least one immunoglobulin Fc region by a covalent bond, and
(b) isolating the protein complex, essentially including the covalently linked physiologically active polypeptide, non-peptidyl polymer, and immunoglobulin Fc region prepared in step (a), in which the non-peptidyl polymer is linked to the N-terminus of the immunoglobulin Fc fragment.

A specific embodiment of the present invention provides the preparation method, in which step (a) comprises:
(a1) preparing a conjugate by linking one end of the non-peptidyl polymer to the immunoglobulin Fc region or the physiologically active polypeptide by a covalent bond; and
(a2) isolating the conjugate prepared in step (a1) and linking the other end of the non-peptidyl polymer of the isolated conjugate to the other of the immunoglobulin Fc region and the physiologically active polypeptide by a covalent bond.

Another specific embodiment of the present invention provides the preparation method in which in step (a1), the reaction mole ratio between the physiologically active polypeptide and the non-peptidyl polymer is in the range from 1:1 to 1:30, and the reaction mole ratio between the immunoglobulin Fc fragment and the non-peptidyl polymer is in the range from 1:1 to 1:20.

Still another specific embodiment of the present invention provides the preparation method in which step (a1) is performed in a pH condition from 4.0 to 9.0.

Still another specific embodiment of the present invention provides the preparation method in which step (a1) is performed at a temperature from 4.0° C. to 25° C.

Still another specific embodiment of the present invention provides the preparation method in which in step (a1), the reaction concentration of the immunoglobulin Fc region or physiologically active polypeptide is in the range from 0.1 mg/mL to 100 mg/mL.

Still another specific embodiment of the present invention provides the preparation method in which in step (a2), the reaction mole ratio between the conjugate and the immunoglobulin Fc region or the physiologically active polypeptide is in the range from 1:0.1 to 1:20.

Still another specific embodiment of the present invention provides the preparation method in which step (a2) is performed in a pH condition from 4.0 to 9.0.

Still another specific embodiment of the present invention provides the preparation method in which step (a2) is performed at a temperature from 4.0° C. to 25° C.

Still another specific embodiment of the present invention provides the preparation method in which in step (a2), the concentration of the immunoglobulin Fc region or physiologically active polypeptide is in the range from 0.1 mg/mL to 100 mg/mL.

Still another specific embodiment of the present invention provides the preparation method in which step (a1) and step (a2) are performed in the presence of a reducing agent.

Still another specific embodiment of the present invention provides the preparation method in which the reducing agent is selected from the group consisting of sodium cyanoborohydride (NaCNBH3), sodium borohydride, dimethylamine borate, and pyridine borate.

Still another specific embodiment of the present invention provides the preparation method in which in step (a2), the isolation is performed by a single or combined purification method selected from the group consisting of anion exchange chromatography, cation exchange chromatography, hydrophobic chromatography, affinity chromatography, and size exclusion chromatography.

Still another specific embodiment of the present invention provides the preparation method in which the functional group of the anion exchange chromatography resin is any one selected from the group consisting of quaternary ammonium (Q), quaternary aminoethyl (QAE), diethylaminoethyl (DEAE), polyethylene amine (PEI), dimethyl-aminoethyl (DMAE), and trimethylaminoethyl (TMAE).

Still another specific embodiment of the present invention provides the preparation method in which the functional group of the cation exchange chromatography resin is any one selected from the group consisting of methylsulfonate (S), sulfopropyl (SP), carboxymethyl (CM), sulfoethyl (SE), and polyaspartic acid.

Still another specific embodiment of the present invention provides the preparation method in which the functional group of the hydrophobic chromatography resin is any one selected from the group consisting of phenyl, octyl, (iso) propyl, butyl, and ethyl.

Still another specific embodiment of the present invention provides the preparation method in which the functional group of the affinity chromatography resin is any one selected from the group consisting of protein A, heparin, blue, benzamidine, metal ions (cobalt, nickel, and copper), and an antibody to a part or the entirety of constituting components of the protein complex, in which both ends of the non-peptidyl polymer are respectively conjugated to the immunoglobulin Fc region and the physiologically active polypeptide.

Still another specific embodiment of the present invention provides the preparation method in which the resin of the size exclusion chromatography is selected from the group consisting of Superdex, Sephacryl, Superpose, and Sephadex.

Still another specific embodiment of the present invention provides the preparation method in which the isolating the protein complex of step (b) is performed by a single or combined method selected from the group consisting of anion exchange chromatography, cation exchange chromatography, hydrophobic chromatography, affinity chromatography, and size exclusion chromatography.

Still another specific embodiment of the present invention provides the preparation method in which the functional group of the anion exchange chromatography resin is any one selected from the group consisting of quaternary ammonium (Q), quaternary aminoethyl (QAE), diethylaminoethyl (DEAE), polyethylene amine (PEI), dimethyl-laminomethyl (DMAE), and trimethylaminoethyl (TMAE).

Still another specific embodiment of the present invention provides the preparation method in which the functional group of the cation exchange chromatography resin is any one selected from the group consisting of methylsulfonate (S), sulfopropyl (SP), carboxymethyl (CM), sulfoethyl (SE), and polyaspartic acid.

Still another specific embodiment of the present invention provides the preparation method in which the functional group of the hydrophobic chromatography resin is any one selected from the group consisting of phenyl, octyl, (iso) propyl, butyl, and ethyl.

Still another specific embodiment of the present invention provides the preparation method in which the functional group of the affinity chromatography resin is any one selected from the group consisting of protein A, heparin, blue, benzamidine, metal ions (cobalt, nickel, and copper), an antibody to a part or the entirety of constituting components of the protein complex, in which both ends of the non-peptidyl polymer are respectively conjugated to the immunoglobulin Fc region and the physiologically active polypeptide.

Still another specific embodiment of the present invention provides the preparation method in which the resin of the size exclusion chromatography is selected from the group consisting of Superdex, Sephacryl, Superpose, and Sephadex.

Still another specific embodiment of the present invention provides the preparation method in which step (b) is to isolate the protein complex in which the non-peptidyl polymer and an immunoglobulin Fc region, constituting a protein complex, are linked through the N-terminus of the immunoglobulin Fc region.

Still another aspect of the present invention provides a method of preparing the position-specific protein complex, the method comprising:

(a') preparing a conjugate by linking one end of the non-peptidyl polymer to the immunoglobulin Fc region or the physiologically active polypeptide by a covalent bond, which is performed in a pH condition from 4.0 to 9.0;

(b') isolating the conjugate prepared in step (a') and linking the other end of the non-peptidyl polymer of the isolated conjugate to the other of the immunoglobulin Fc region and the physiologically active polypeptide by a covalent bond, which is performed in a pH condition from 4.0 to 9.0; and (c') isolating the protein complex, essentially including the covalently linked physiologically active polypeptide, non-peptidyl polymer, and immunoglobulin Fc region prepared in step (b'), in which the non-peptidyl polymer is linked to the N-terminus of the immunoglobulin Fc fragment.

In particular, an important condition for a reaction rate in binding between the non-peptidyl polymer and the N-terminus of the immunoglobulin Fc region is pH, and the site-specific binding may occur well at a pH value below neutral pH, that is, below pH 7.0.

The linking of the non-peptidyl polymer to the N-terminus of the immunoglobulin Fc region is performed at a pH value below neutral pH, but suitably performed at a weak acidic to acidic pH which does not denature a tertiary structure or activity of the protein, but is not limited thereto. As a non-limiting example, the immunoglobulin Fc region used in the present invention has an amino acid sequence of SEQ ID NO: 2 and it was confirmed to have N-terminal specificity at a weak basic condition of about pH 8.2 (Example 5).

That is, when a general immunoglobulin Fc region is used, the reaction rate of specific binding of N-terminal of the immunoglobulin Fc region and the non-peptidyl polymer is increased at a pH below neutral pH. However, when an immunoglobulin Fc region mutated to have a lower pH sensitivity is used, the reaction rate of the binding may not be restricted to the condition.

Still another aspect of the present invention provides a method of preparing the protein complex, the method comprising:

(a') preparing a conjugate by linking one end of the non-peptidyl polymer to any one of the immunoglobulin Fc region and the physiologically active polypeptide by a covalent bond, in which the reaction mole ratio between the physiologically active polypeptide and the non-peptidyl polymer is in the range from 1:1 to 1:30, and the reaction mole ratio between the immunoglobulin Fc region and the non-peptidyl polymer is in the range from 1:1 to 1:20, a reducing agent is contained in the range from 1 mM to 100 mM, and the reaction is performed in the condition of pH from 4.0 to 9.0, at a temperature from 4.0° C. to 25° C., and the reaction concentration of the immunoglobulin Fc region or physiologically active polypeptide is in the range from 0.1 mg/mL to 100 mg/mL;

(b') isolating the conjugate prepared in step (a') and linking the other end of the non-peptidyl polymer of the isolated conjugate to the other of the immunoglobulin Fc region and the physiologically active polypeptide by a covalent bond, in which the reaction mole ratio between the conjugate and the immunoglobulin Fc region or the physiologically active polypeptide is in the range from 1:0.1 to 1:20, a reducing agent is contained in the range from 1 mM to 100 mM, and the reaction is performed in the condition of pH from 4.0 to 9.0, at a temperature from 4.0° C. to 25° C., and the reaction concentration of the immunoglobulin Fc region or physiologically active polypeptide is in the range from 0.1 mg/mL to 100 mg/mL; and (c') isolating the protein complex, essentially comprising the covalently linked physiologically active polypeptide, non-peptidyl polymer, and immunoglobulin Fc region prepared in step (b'), in which the non-peptidyl polymer is linked to the N-terminus of the immunoglobulin Fc fragment.

Still another specific embodiment of the present invention provides a method for preparing the protein complex with N-terminal selectivity of 90% or higher.

Still another aspect of the present invention provides a pharmaceutical composition for improving in vivo duration and stability of the physiologically active polypeptide comprising the protein complex as an active ingredient.

A specific embodiment of the present invention provides a composition comprising the protein complex in an amount of 90% or higher.

Definitions

As used herein, the term "protein complex" or "complex" refers to a structure in which at least one physiologically active polypeptide, at least one non-peptidyl polymer having a reactive group at both ends thereof, and at least one immunoglobulin Fc region are linked to each other via a covalent bond. Further, a structure in which only two molecules selected from the physiologically active polypeptide, the non-peptidyl polymer, and the immunoglobulin Fc region are linked to each other via a covalent bond is called "conjugate" in order to distinguish it from the "complex."

The protein complex of the present invention may be a protein complex in which the PEG is linked to the modified G-CSF and the immunoglobulin Fc region through reactive groups at both ends thereof by a covalent bond, respectively.

As used herein, the term "physiologically active polypeptide," "physiologically active protein," "active protein," or "protein drug" refers to a polypeptide or a protein having some kind of antagonistic activity to a physiological event in vivo, and these terms may be used interchangeably.

As used herein, the term "non-peptidyl polymer" refers to a biocompatible polymer including two or more repeating units which are linked to each other by any covalent bond excluding a peptide bond, but is not limited thereto.

As used herein, the term "immunoglobulin Fc region" refers to a region of an immunoglobulin molecule, except for the variable regions of the heavy and light chains, the heavy-chain constant region 1 (CH1) and the light-chain constant region 1 (CL1) of an immunoglobulin. The immunoglobulin Fc region may further include a hinge region at the heavy-chain constant region. In particular, the immunoglobulin Fc region of the present invention may be a fragment, including a part or all of the Fc region, and in the present invention, the immunoglobulin Fc region may be used interchangeably with an immunoglobulin fragment.

A native Fc has a sugar chain at position Asn297 of heavy-chain constant region 1, but *E. coli*-derived recombinant Fc is expressed as an aglycosylated form. The removal of sugar chains from Fc results in a decrease in binding affinity of Fc gamma receptors 1, 2, and 3 and complement (C1q) to heavy-chain constant region 1, leading to a decrease or loss in antibody-dependent cell-mediated cytotoxicity or complement-dependent cytotoxicity.

As used herein, the term "immunoglobulin constant region" may refer to an Fc fragment including heavy-chain constant region 2 (CH2) and heavy-chain constant region 3 (CH3) (or containing heavy-chain constant region 4 (CH4)), except for the variable regions of the heavy and light chains, the heavy-chain constant region 1 (CHI) and the light-chain constant region (CL) of an immunoglobulin, and may further include a hinge region at the heavy chain constant region. Further, the immunoglobulin constant region of the present invention may be an extended immunoglobulin constant region including a part or all of the Fc region including the heavy-chain constant region 1 (CH1) and/or the light chain constant region (CL), except for the variable regions of the heavy and light chains of an immunoglobulin, as long as it has a physiological function substantially similar to or better than the native protein.

Meanwhile, the immunoglobulin constant region may originate from humans or animals, such as cows, goats, pigs, mice, rabbits, hamsters, rats, guinea pigs, etc., and may preferably be of human origin. In addition, the immunoglobulin constant region may be selected from constant regions derived from IgG, IgA, IgD, IgE, IgM, or combinations or hybrids thereof, preferably, derived from IgG or IgM, which are the most abundant thereof in human blood, and most preferably, derived from IgG, which is known to improve the half-life of ligand-binding proteins. In the present invention, the immunoglobulin Fc region may be a dimer or multimer consisting of single-chain immunoglobulins of domains of the same origin.

As used herein, the term "combination" means that polypeptides encoding single-chain immunoglobulin constant regions (preferably Fc regions) of the same origin are linked to a single-chain polypeptide of a different origin to form a dimer or multimer. That is, a dimer or a multimer may be prepared from two or more fragments selected from the group consisting of Fc fragments of IgG Fc, IgA Fc, IgM Fc, IgD Fc, and IgE Fc.

As used herein, the term "hybrid" means that sequences encoding two or more immunoglobulin constant regions of different origins are present in a single-chain of an immunoglobulin constant region (preferably, an Fc region). In the present invention, various hybrid forms are possible. For example, the hybrid domain may be composed of one to four domains selected from the group consisting of CH1, CH2, CH3, and CH4 of IgG Fc, IgM Fc, IgA Fc, IgE Fc, and IgD Fc, and may further include a hinge region.

IgG may be divided into the IgG1, IgG2, IgG3, and IgG4 subclasses, and the present invention may include combinations or hybrids thereof. Preferred are the IgG2 and IgG4 subclasses, and most preferred is the Fc region of IgG4 rarely having effector functions such as complement dependent cytotoxicity (CDC).

The immunoglobulin constant region may have the glycosylated form to the same extent as, or to a greater or lesser extent than the native form or maybe the deglycosylated form. Increased or decreased glycosylation or deglycosylation of the immunoglobulin constant region may be achieved by typical methods, for example, by using a chemical method, an enzymatic method, or a genetic engineering method using microorganisms. Herein, when deglycosylated, the complement (C1q) binding to an immunoglobulin constant region becomes significantly decreased, and antibody-dependent cytotoxicity or complement-dependent cytotoxicity is reduced or removed, thereby not inducing unnecessary immune responses in vivo. In this context, deglycosylated or aglycosylated immunoglobulin constant regions are more consistent with the purpose of drug carriers. Accordingly, the immunoglobulin Fc region may be more specifically an aglycosylated Fc region derived from human IgG4, that is, a human IgG4-derived aglycosylated Fc region. The human-derived Fc region is more preferable than a non-human derived Fc region, which may act as an antigen in the human body and cause undesirable immune responses such as the production of a new antibody against the antigen.

Further, the immunoglobulin constant region of the present invention includes not only the native amino acid sequence but also sequence derivatives (mutants) thereof. The amino acid sequence derivative means that it has an amino acid sequence different from the wild-type amino acid sequence as a result of deletion, insertion, conserved or non-conserved substitution of one or more amino acid residues, or a combination thereof. For instance, amino acid residues at positions 214 to 238, 297 to 299, 318 to 322, or 327 to 331 in IgG Fc, known to be important for linkage, may be used as the sites suitable for modification. Various derivatives, such as those prepared by removing the sites capable of forming disulfide bonds, removing several N-terminal amino acids from native Fc, or adding methionine to the N-terminus of native Fc, may be used. In addition, complement fixation sites, e.g., C1q fixation sites, or ADCC sites, may be eliminated to remove the effector function. The techniques of preparing the sequence derivatives of the immunoglobulin constant region are disclosed in International Patent Publication Nos. WO 97/34631 and WO 96/32478.

Amino acid substitutions in a protein or peptide molecule that do not alter the activity of the molecule are well known in the art (H. Neurath, R. L. Hill, The Proteins, Academic Press, New York, 1979). The most common substitutions occur between amino acid residues Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu, and Asp/Gly, in both directions. Optionally, amino acids may be modified by phosphorylation, sulfation, acrylation, glycosylation, methylation, farnesylation, acetylation, amidation, or the like.

The above-described immunoglobulin constant region derivative may be a derivative which has a biological activity equivalent to that of the immunoglobulin constant region of the present invention, but has increased structural stability of the immunoglobulin constant region against heat, pH, etc. Further, the immunoglobulin constant region may be obtained from a native type isolated from humans or animals such as cows, goats, pigs, mice, rabbits, hamsters, rats, guinea pigs, etc., or may be their recombinants or derivatives obtained from transformed animal cells or microorganisms. Herein, they may be obtained from a native immunoglobulin by isolating whole immunoglobulins from human or animal organisms and treating them with a proteolytic enzyme. Papain digests the native immunoglobulin into Fab and Fc regions, and pepsin treatment results in the production of pF'c and F(ab)2 fragments. These fragments may be subjected, for example, to size exclusion chromatography to isolate Fc or pFc.

Preferably, a human-derived immunoglobulin constant region may be a recombinant immunoglobulin constant region that is obtained from a microorganism.

The protein complex of the present invention may include one or more of a unit structure of a [physiologically active polypeptide/non-peptidyl polymer/immunoglobulin Fc region], in which all components may be linked in a linear form by a covalent bond. The non-peptidyl polymer may have a reactive group at both ends thereof and is linked to the physiologically active polypeptide and the immunoglobulin Fc region through the reactive group by a covalent bond, respectively. That is, at least one conjugate of the physiologically active polypeptide and the non-peptidyl polymer is linked to one immunoglobulin Fc region by a covalent bond, thereby forming a monomer, dimer, or multimer of the physiologically active polypeptide, which is mediated by the immunoglobulin Fc region. Therefore, an increase in vivo activity and stability may be more effectively achieved.

The reactive group at both ends of the non-peptidyl polymer is preferably selected from the group consisting of a reactive aldehyde group, a propionaldehyde group, a butyraldehyde group, a maleimide group, and a succinimide derivative. The succinimide derivative may be hydroxy succinimidyl, succinimidyl carboxymethyl, succinimidyl valerate, succinimidyl methyl butanoate, succinimidyl methyl propionate, succinimidyl butanoate, succinimidyl propionate, N-hydroxysuccinimide, or succinimidyl carbonate. In particular, when the non-peptidyl polymer has a reactive aldehyde group at both ends, it is effective in linking both of the ends with the physiologically active polypeptide and the immunoglobulin with minimal non-specific reactions. A final product generated by reductive alkylation by an aldehyde bond is much more stable than when linked by an amide bond.

The reactive groups at both ends of the non-peptidyl polymer of the present invention may be the same as or different from each other. The non-peptide polymer may possess aldehyde reactive groups at both ends, or it may possess an aldehyde group at one end and a maleimide reactive group at the other end, or an aldehyde group at one end and a succinimide reactive group at the other end, but is not limited thereto.

For example, the non-peptide polymer may possess a maleimide group at one end and an aldehyde group, a propionaldehyde group, or a butyraldehyde group at the other end. Also, the non-peptide polymer may possess a succinimidyl group at one end and a propionaldehyde group, or a butyraldehyde group at the other end. When a polyethylene glycol having a reactive hydroxy group at both ends thereof is used as the non-peptidyl polymer, the hydroxy group may be activated to various reactive groups by known chemical reactions, or a commercially available polyethylene glycol having a modified reactive group may be used so as to prepare the protein complex of the present invention.

When the physiologically active polypeptide and the immunoglobulin Fc region are linked via the non-peptidyl polymer, each of both of the ends of the non-peptidyl polymer may bind to the N-terminus of the immunoglobulin Fc region and the N-terminus (amino terminus), C-terminus (carboxy terminus), or free reactive group of a lysine residue, a histidine residue, or a cysteine residue of the physiologically active polypeptide.

As used herein, the term "N-terminus" refers to an N-terminus of a peptide, which is a site to which a linker including a non-peptidyl polymer can be conjugated for the purpose of the present invention. Examples of the N-terminus may include not only amino acid residues at the distal end of the N-terminus, but but also amino acid residues near the N-terminus, but are not limited thereto. Specifically, the 1st to the 20th amino acid residues from the distal end may be included.

The non-peptidyl polymer of the present invention may be selected from the group consisting of polyethylene glycol, polypropylene glycol, copolymers of ethylene glycol and propylene glycol, polyoxyethylated polyols, polyvinyl alcohol, polysaccharides, dextran, polyvinyl ethyl ether, biodegradable polymers such as PLA (polylactic acid) and PLGA (polylactic-glycolic acid), lipid polymers, chitins, hyaluronic acid, and combinations thereof, and specifically, polyethylene glycol, but is not limited thereto. Also, derivatives thereof well known in the art and easily prepared within the skill of the art are included in the non-peptidyl polymer of the present invention. The non-peptidyl polymer may have a molecular weight in the range of 1 kDa to 100 kDa, and specifically 1 kDa to 20 kDa.

The physiologically active polypeptide of the present invention may be exemplified by various physiologically active polypeptides such as hormones, cytokines, interleukins, interleukin-binding proteins, enzymes, antibodies, growth factors, transcription factors, blood factors, vaccines, structural proteins, ligand proteins or receptors, cell surface antigens, receptor antagonists, and derivatives or analogs thereof.

Specifically, the physiologically active polypeptide includes human growth hormones, growth hormone-releasing hormones, growth hormone-releasing peptides, interferons and interferon receptors (e.g., interferon-alpha, -beta, and -gamma, soluble type I interferon receptors), colony-stimulating factors, interleukins (e.g., interleukin-1, -2, -3, -4, -6, -7, -8, -9, -10, -11, -12, -13, -14, -15, -16, -17, -18, -19, -20, -21, -22, -23, -24, -25, -26, -27, -28, -29. -30. Etc.), and interleukin receptors (e.g; IL-1 receptor. IL-4 receptor, etc.), enzymes (e.g., glucocerebrosidase, iduronate-2-sulfatase, alpha-galactosidase-A, agalsidase alpha, beta, alpha-L-iduronidase, butyrylcholinesterase, chitinase, glutamate decarboxylase, imiglucerase, lipase, uricase, platelet-activating factor acetylhydrolase, neutral endopeptidase, myeloperoxidase, etc.), interleukin- and cytokine-binding proteins (e.g., IL-18 bp, TNF-binding protein, etc.), macrophage-activating factors, macrophage peptides, B-cell factors, T-cell factors, protein A, allergy inhibitors, cell necrosis glycoproteins, immunotoxins, lymphotoxins, tumor necrosis factor, tumor suppressors, transforming growth factor, alpha-1 anti-trypsin, albumin, alpha-lactalbumin, apolipoprotein-E, erythropoietin, glycosylated crythropoictin, angiopoietins, hemoglobin, thrombin, thrombin receptors activating peptides, throm-bomodulin, blood factors VII, VIIa, VIII, IX, and XIII, plasminogen activators, fibrin-binding peptides, urokinase, streptokinase, hirudin, protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone-stimulating protein, calcitonin, insulin, oxyntomodulin, glucagon, glucagon derivatives, glucagon-like peptides, exendins (Exendin4), atriopeptin, cartilage-inducing factor, elcatonin, connective tissue-activating factor, tissue factor pathway inhibitor, follicle-stimulating hormone, luteinizing hormone, luteinizing hormone-releasing hormone, nerve growth factors (e.g., nerve growth factor, cilliary neurotrophic factor, axogenesis factor-1, brain-natriuretic peptide, glial-derived neurotrophic factor, netrin, neutrophil inhibitor factor, neurotrophic factor, neurturin, etc.), parathyroid hormone, relaxin, secretin, somatomedin, insulin-like growth factor, adrenocortical hormone, glucagon, cholecystokinin, pancreatic polypeptide, gastrin-releasing peptide, corticotrophin-releasing factor, thyroid-stimulating hormone, autotaxin, lactoferrin, myostatin, receptors (e.g., TNFR (P75), TNFR (P55), IL-1 receptor, VEGF receptor, B-cell-activating factor receptor, etc.), receptor antagonists (e.g., IL1-Ra, etc.), cell surface antigens (e.g., CD 2, 3, 4, 5, 7, 11a, 11b, 18, 19, 20, 23, 25, 33, 38, 40, 45, 69, etc.), monoclonal antibodies, polyclonal antibodies, antibody fragments (e.g., scFv, Fab, Fab', F(ab')2, and Fd), and virus-derived vaccine antigens.

Specifically, the physiologically active polypeptide of the present invention may be granulocyte colony-stimulating factor, erythropoietin, or modified versions thereof. In the preferred embodiment, the polypeptide is G-CSF.

In the present invention, the antibody fragment may be Fab, Fab', F(ab'), Fd, or scFv having an ability to bind to a specific antigen, and preferably, Fab.' The Fab fragments include the variable domain (VL) and constant domain (CL) of the light chain and the variable domain (VH) and the first constant domain (CH1) of the heavy chain. The Fab' fragments differ from the Fab fragments in terms of the addition of several amino acid residues including one or more cysteine residues from the hinge region at the carboxyl terminus of the CH1 domain. The Fd fragments are fragments consisting of only the VH and CH1 domains, and the F(ab')2 fragments are produced by binding of two molecules of Fab' fragments by either disulfide bonding or a chemical reaction. The scFv fragment is a single polypeptide chain, in which only VL and VH domains are linked to each other by a peptide linker Further, the protein complex of the present invention may be used in the development of long-acting protein formulations of animal growth hormone such as bovine growth hormone or porcine growth hormone, and long-acting protein formulations for treatment or prevention of animal disease, such as interferon. The preferred protein complex according to the present invention is a $Ser^{17}$, $^{65}$-GCSF-polyethylene glycol-IgG4-Fc which is the conjugate of a recombinant human GCSF analog and human IgG4-Fc fragment connected via two chemical bonds between an amino group of N-terminus in each protein and one molecule of polyethylene glycol dialdehyde having the molecular weight of 72 kDa.

Another aspect of the present invention provides a method of preparing the protein complex of the present invention. In particular, the present invention provides a method of preparing a position-specific protein complex, the method comprising: (a) preparing a protein complex by linking at least one non-peptidyl polymer having a reactive group at both ends, at least one physiologically active polypeptide, and at least one immunoglobulin Fc region by a covalent bond, and (b) isolating the protein complex, essentially including the covalently linked physiologically active polypeptide, non-peptidyl polymer, and immunoglobulin Fc region prepared in step (a), in which the non-peptidyl polymer is linked to the N-terminus of the immunoglobulin Fc fragment.

The immunoglobulin Fc region of the present invention may be in the form of a dimer, or in the form of a homodimer or heterodimer. Therefore, the immunoglobulin Fc region constituting the protein complex of the present invention may include one or two or more of an N-terminus. Thus, the immunoglobulin Fc region may be linked to at least one non-peptidyl polymer via the N-terminus. In particular, the immunoglobulin Fc region of the present invention may be in the form of a homodimer, and therefore, linked to one or two non-peptidyl polymers via two N-terminals included in the homodimer of the immunoglobulin Fc region. In this regard, the non-peptidyl polymers may bind to the physiologically active polypeptides, respectively, thereby forming the protein complex.

Accordingly, the protein complex of the present invention may be prepared by linking one or two or more of the non-peptidyl polymer, one or two or more of the physiologically active polypeptide, and one or two or more of the immunoglobulin Fc region via a covalent bond.

In step (a), the covalent bonds between the three components may occur sequentially or at the same time. For example, when the physiologically active polypeptide and the immunoglobulin Fc region are linked to both ends of the non-peptidyl polymer, respectively, any one of the physiologically active polypeptide and the immunoglobulin Fc region may be first linked to one end of the non-peptidyl polymer, and then the other may be linked to the other end of the non-peptidyl polymer. This method is advantageous in that production of by-products other than the desired protein complex is minimized, and the protein complex is prepared in high purity.

Therefore, step (a) may comprise:
(i) linking a specific site of the immunoglobulin Fc region or the physiologically active polypeptide to one end of the non-peptidyl polymer via a covalent bond;
(ii) homogeneously isolating a conjugate from the reaction mixture, in which the conjugate is prepared by linking the specific site of the immunoglobulin Fc region or the physiologically active polypeptide to the non-peptidyl polymer; and
(iii) producing a protein complex by linking the physiologically active polypeptide or the specific site of the immunoglobulin Fc region to the other end of the non-peptidyl polymer of the isolated conjugate.

Meanwhile, in the present invention, step (a) includes (a1) preparing a conjugate by linking one end of the non-peptidyl polymer to any one of the immunoglobulin Fc region and the physiologically active polypeptide by a covalent bond; and (a2) isolating the conjugate prepared in step (a1) and linking the other end of the non-peptidyl polymer of the isolated conjugate to the other of the physiologically active polypeptide and the immunoglobulin Fc region by a covalent bond.

Specifically, step (a) may comprise (a1') preparing a conjugate by linking one end of the non-peptidyl polymer to the immunoglobulin Fc region by a covalent bond; and (a2') isolating the conjugate prepared in step (a1') and linking the other end of the non-peptidyl polymer of the isolated conjugate to the physiologically active polypeptide by a covalent bond.

Alternatively, step (a) may include (a1") preparing a conjugate by linking one end of the non-peptidyl polymer to the physiologically active polypeptide by a covalent bond; and (a2") isolating the conjugate prepared in step (a1") and linking the other end of the non-peptidyl polymer of the isolated conjugate to the immunoglobulin Fc region by a covalent bond.

In step (a1), (a1'), or (a1") of the present invention, the reaction mole ratio between the physiologically active polypeptide and the non-peptidyl polymer may be in the range from 1:1 to 1:30, and the reaction mole ratio between the immunoglobulin Fc region and the non-peptidyl polymer may be in the range from 1:1 to 1:20.

Specifically, in step (a1), the reaction mole ratio between the immunoglobulin Fc region and the non-peptidyl polymer may be in the range from 1:1 to 1:20, and in particular, in the range from 1:1 to 1:15, 1:1 to 1:10, or 1:1 to 1:4. In step (a1"), the reaction mole ratio between the physiologically active polypeptide and the non-peptidyl polymer may be in the range from 1:1 to 1:30, and in particular, in the range from 1:1 to 1:15 or 1:1 to 1:10. A preparation yield and cost may be optimized depending on the reaction mole ratio.

In the present invention, step (a1), (a1'), or (a1") may be performed in a pH condition from 4.0 to 9.0; step (a1), (a1'), or (a1") may be performed at a temperature from 4.0° C. to 25° C.; in step (a1), (a1'), or (a1"), the reaction concentration of the immunoglobulin Fc region or physiologically active polypeptide may be in the range from 0.1 mg/mL to 100 mg/mL.

In step (a2), (a2'), or (a2") of the present invention, the reaction mole ratio between the conjugate and the immunoglobulin Fc region or the physiologically active polypeptide may be in the range from 1:0.1 to 1:20, and in particular, in the range from 1:0.2 to 1:10. Specifically, in step (a2'), the reaction mole ratio between the conjugate and the physiologically active polypeptide may be in the range from 1:0.1 to 1:20, and in step (a2"), the reaction mole ratio between the conjugate and the immunoglobulin Fc region may be in the range from 1:0.1 to 1:20. A preparation yield and cost may be optimized depending on the reaction mole ratio.

In the present invention, step (a2), (a2'), or (a2") may be performed in a pH condition from 4.0 to 9.0; step (a2), (a2'), or (a2") may be performed at a temperature from 4.0° C. to 25° C.; in step (a2), (a2'), or (a2"), the reaction concentration of the immunoglobulin Fc region or physiologically active polypeptide may be in the range from 0.1 mg/mL to 100 mg/mL.

Meanwhile, the preparation method of the present invention may be a method of preparing a position-specific protein complex, including (a') preparing a conjugate by linking one end of the non-peptidyl polymer to any one of the immunoglobulin Fc region and the physiologically active polypeptide by a covalent bond, in which the reaction mole ratio between the physiologically active polypeptide and the non-peptidyl polymer is in the range from 1:1 to 1:30, the reaction mole ratio between the immunoglobulin Fc region and the non-peptidyl polymer is in the range from 1:1 to 1:20, a reducing agent is contained in the range from 1 mM to 100 mM, the reaction is performed in the condition of pH from 4.0 to 9.0, at a temperature from 4.0° C. to 25° C., and the reaction concentration of the immunoglobulin Fc region or physiologically active polypeptide is in the range from 0.1 mg/mL to 100 mg/mL;
(b') isolating the conjugate prepared in step (a') and linking the other end of the non-peptidyl polymer of the isolated conjugate to the other of the immunoglobulin Fc region and the physiologically active polypeptide by a covalent bond, in which the reaction mole ratio between the conjugate and the immunoglobulin Fc region or the physiologically active polypeptide is in the range from 1:0.1 to 1:20, a reducing agent is contained in the range from 1 mM to 100 mM, the reaction is performed in the condition of pH from 4.0 to 9.0, at a temperature from 0° C. to 25° C., and the concentration of the immunoglobulin Fc region or physiologically active polypeptide is in the range from 0.1 mg/mL to 100 mg/mL; and
(c') isolating the protein complex, essentially including the covalently linked physiologically active polypeptide, non-peptidyl polymer, and immunoglobulin Fc region prepared in step (b'), in which the non-peptidyl polymer is linked to the N-terminus of the immunoglobulin Fc fragment, but is not limited thereto.

The reactions in step (a1), step (a1'), step (a1"), step (a2), step (a2'), and step (a2") of the present invention may be performed in the presence of a reducing agent, considering the type of the reactive groups at both ends of the non-peptidyl polymer which participate in the reactions, if necessary. The reducing agent of the present invention may be sodium cyanoborohydride (NaCNBH3), sodium borohydride, dimethylamine borate, or pyridine borate. In this regard, a concentration of the reducing agent (e.g., sodium cyanoborohydride), temperature and pH of a reaction solution, and total concentrations of the physiologically active polypeptide and the immunoglobulin Fc region participating in the reaction are important in terms of production yield and purity. To maximize the production of a high-purity homogeneous complex, various combinations of the conditions are needed. According to the feature of the physiologically active polypeptide to be prepared, various conditions are possible, but not limited to, the reducing agent (e.g., sodium cyanoborohydride) may be contained in the range from 1 mM to 100 mM, the reaction solution may be at a temperature from 0° C. to 25° C. and in the condition of pH from 4.0 to 9.0, and the concentration of the reaction protein (concentration of the immunoglobulin Fc region or physiologically active polypeptide included upon the reaction) may be in the range from 5 mg/mL to 100 mg/mL.

Meanwhile, the separation of the conjugate in step (a2), step (a2'), and step (a2") may be performed, if necessary, by a method selected from general methods which are used in protein separation, considering the properties such as purity, hydrophobicity, molecular weight, and electrical charge which are required for the separated conjugate. For example, the separation may be performed by applying various known methods, including size exclusion chromatography, affinity chromatography, hydrophobic chromatography, or ion exchange chromatography, and if necessary, a plurality of different methods are used in combination to purify the conjugate with higher purity.

According to the features of the physiologically active polypeptide to be prepared, various conditions are possible. However, in order to separate the immunoglobulin Fc region or the physiologically active polypeptide conjugate linked to the non-peptidyl polymer, size exclusion chromatography is generally performed. For further scale-up and separation of isomers generated by binding of the non-peptidyl polymer at a position other than the desired position or a small amount of denatured forms generated during preparation, affinity chromatography, hydrophobic chromatography, or ion exchange chromatography may also be used.

In the present invention, step (b) may be performed, if necessary, by a method selected from general methods which are used in protein separation, considering the properties such as hydrophobicity, molecular weight, and electrical charge, in order to finally purify a high-purity complex. For example, the separation may be performed by applying various known methods, including size exclusion chromatography, affinity chromatography, hydrophobic chromatography, or ion exchange chromatography, and if necessary, a plurality of different methods are used in combination to purify the complex with higher purity. According to the features of the desired complex consisting of the physiologically active polypeptide, the non-peptidyl polymer, and the Fc constant region, various separation conditions are possible. However, in order to separate the complex in which the physiologically active polypeptide and the immunoglobulin Fc region are respectively linked to both ends of the non-peptidyl polymer, size exclusion chromatography is generally performed. For further scale-up and effective separation of isomers or side-reaction products generated by binding of the physiologically active polypeptide or the immunoglobulin Fc region, and non-peptidyl polymer at a position other than the desired position, or a small amount of denatured forms generated during preparation, unreacted physiologically active polypeptide, non-peptidyl polymer, and immunoglobulin Fc region, hydrophobic chromatography, ion exchange chromatography, or affinity chromatography may be used in combination. In particular, hydrophobic chromatography and ion exchange chromatography may be used in combination, and a plurality of hydrophobic chromatography or a plurality of ion exchange chromatography is also possible. According to the complex to be prepared, ion exchange chromatography or hydrophobic chromatography may be used singly.

In the present invention, the ion exchange chromatography is to separate a protein by passing charged protein at a specific pH through a charged ion resin-immobilized chromatography column and separating the protein by a difference in the migration rate of the protein, and it may be anion exchange chromatography or cation exchange chromatography.

The anion exchange chromatography is to use a cation resin, and a functional group of the resin constituting the corresponding anion exchange chromatography may be any one selected from the group consisting of quaternary ammonium (Q), quaternary aminoethyl (QAE), diethylaminoethyl (DEAE), polyethylene amine (PEI), dimethyl-laminomethyl (DMAE), and trimethylaminoethyl (TMAE), but is not limited thereto.

Further, the cation exchange chromatography is to use an anion resin, and a functional group of the resin constituting the corresponding cation exchange chromatography may be any one selected from the group consisting of methylsulfonate (S), sulfopropyl (SP), carboxymethyl (CM), sulfoethyl (SE), and polyaspartic acid, but is not limited thereto.

In the present invention, a functional group of the resin constituting the hydrophobic chromatography may be any one selected from the group consisting of phenyl, octyl, (iso)propyl, butyl, and ethyl, but is not limited thereto.

In the present invention, a functional group of the resin constituting the size exclusion chromatography may be any one selected from the group consisting of Superdex, Sephacryl, Superpose, and Sephadex, but is not limited thereto.

Furthermore, the affinity chromatography in the present invention is to separate a protein by a difference in the migration rate of the protein, which is caused by the interaction between the protein and a ligand capable of interacting with the protein in a resin onto which the ligand is immobilized. A functional group of the resin constituting the affinity chromatography may be any one selected from the group consisting of protein A, heparin, blue, benzamidine, metal ions (cobalt, nickel, and copper), and an antibody to a part or the entirety of the constituting components of the protein complex, in which both ends of the non-peptidyl polymer are respectively conjugated to the immunoglobulin Fc region and the physiologically active polypeptide, but is not limited thereto.

In the present invention, step (b) is to isolate the protein complex in which the non-peptidyl polymer and the immunoglobulin Fc region are linked to each other via the N-terminus of the immunoglobulin Fc region.

Still another aspect of the present invention provides a method for preparing a protein complex with N-terminal selectivity of 90% or higher. Specifically, the protein complex prepared by the method of the present invention may be one, in which one end of the non-peptidyl polymer may be linked to the N-terminus of the immunoglobulin Fc region with N-terminal selectivity of 90% or higher, more specifically 95% or higher, even more specifically 98% or higher, and yet even more specifically 99% or higher, but is not limited thereto.

As used herein, the term "linking with N-terminal selectivity of 90% or higher" means that, in 90% or more of the protein complex prepared by purification of the protein complex fractions obtained by a series of reactions according to the present invention, the non-peptidyl polymer is linked to the N-terminus of the Fc region in a position-specific manner. As used herein, the term "90% or higher" may refer to v/v, w/w, and peak/peak, but is not limited to a particular unit. The yield of the protein complex comprising the non-peptidyl polymer linked to the N-terminus of the Fc region in a position-specific manner may vary by reaction conditions, a reactor of the non-peptidyl polymer, etc.

In Examples of the present invention, it was confirmed that a protein complex with N-terminal selectivity of 90% or higher can be prepared by the method according to the present invention, via preparation of various physiologically active polypeptides, non-peptidyl polymers, and Fc complexes.

The pharmaceutical composition may comprise a protein complex, which includes the physiologically active polypeptide-non-peptidyl polymer-N-terminus of an immunoglobulin Fc region, in an amount of 90% or higher, more specifically 95% or higher, even more specifically 98% or higher, and yet even more specifically 99% or higher, but is not limited thereto. As used herein, the term "90% or higher" may refer to v/v, w/w, and peak/peak, but is not limited to a particular unit.

The pharmaceutical composition may further include a pharmaceutically acceptable excipient.

The pharmaceutical composition of the present invention may be administered via various routes including oral, percutaneous, subcutaneous, intravenous, and intramuscular routes, preferably, in the form of an injectable formulation. Further, the pharmaceutical composition of the present invention may be formulated by a method known in the art in order to provide rapid, long-lasting, or delayed release of the active ingredient after administration thereof to a mammal. The formulation may be a tablet, a pill, a powder, a sachet, an elixir, a suspension, an emulsion, a solution, a syrup, an aerosol, a soft or hard gelatin capsule, a sterile injectable solution, or a sterile powder. Examples of suitable carriers, excipients, and diluents may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. The pharmaceutical composition may further include a filler, an anticoagulant, a lubricant, a wetting agent, a flavoring agent, an emulsifying agent, a preservative, etc.

A practical administration dose of the protein complex of the present invention may be determined by several related factors including the types of diseases to be treated, administration routes, the patient's age, gender, weight, and severity of the illness, as well as by the types of the physiologically active polypeptide as an active component. Since the protein complex of the present invention has excellent blood duration and in vivo potency, it can remarkably reduce the administration dose and frequency of a peptide drug, including the protein complex of the present invention.

Still another aspect of the present invention provides a population of protein complexes, including the protein complex prepared according to the above method in an amount of 90% or higher. As used herein, the terms "population of complex", and "population" may be used interchangeably, and they refer to a group of protein complexes including protein complexes, in which a non-peptidyl polymer is linked to the N-terminus of an Fc region, and/or protein complexes, in which a non-peptidyl polymer is linked to a region other than the N-terminus of an Fc region.

The population may include only the protein complexes, in which a non-peptidyl polymer is linked to the N-terminus of an Fc region, or the protein complexes, in which a non-peptidyl polymer is linked to a region other than the N-terminus of an Fc region. Specifically, the percentage of the protein complexes, in which a non-peptidyl polymer is linked to a region other than the N-terminus of an Fc region, included in the population may be 90% or higher, more specifically 95% or higher, even more specifically 98% or higher, and yet even more specifically 99% or higher, but is not limited thereto. As used herein, the term "90% or higher" may refer to v/v, w/w, and peak/peak, but is not limited to a particular unit.

For the purpose of the present invention, the population may refer to a population with an increased percentage of the protein complexes, in which a non-peptidyl polymer is linked to a region other than the N-terminus of an Fc region, by removing impurities, unreacted materials, etc., from the protein complexes prepared thereof. Additionally, the population may refer to one which was prepared by a method for preparing protein complexes with N-terminal selectivity of 90% or higher, but is not limited thereto. The population may be efficiently purified by the method of the present invention.

The present invention is particularly directed to the use of the above-described protein complexes in preventing, alleviating, or treating patient in need thereof having a need in increasing their white blood cell production, count, or are in need of increasing stem cell production by administering to the patient a therapeutically effective amount of a protein complex comprising a modified human granulocyte-colony stimulating factor (hG-CSF) covalently linked to an immunoglobulin Fc region via a non-peptidyl polymer, wherein the non-peptidyl polymer is site-specifically linked to an N-terminus of the immunoglobulin Fc region, and the modified hG-CSF comprises substitutions in at least one of Cys17 and Pro65. Such methodologies may or may not be in combination with chemotherapeutic agents or regimens including docetaxel, doxorubicin, cyclophosphamide (TAC); dose-dense doxorubicin plus cyclophosphamide (AC), with or without subsequent weekly or semiweekly paclitaxel; and docetaxel plus cyclophosphamide (TC). Regardless, the methodologies described in this invention provides superior clinical and side effect outcomes for patients receiving such a regimen. In preferred embodiments, at least one dose of EFLAPEGRASTIM is administered at 13.2 mg/0.6 mL (containing 3.6 mg G-CSF) fixed-dose to the patient within about 26 hours, 24 hours, 22 hours, 18 hours, 12 hours, 6 hours, about 5 hours, 2 hours, 1 hour or half an hour of the completion of chemotherapy. In one embodiment, TC is administered on Day 1 of each cycle intravenously (IV). Accordingly, Docetaxel is administered at 75 mg/m$^2$ IV infusion and (ii) Cyclophosphamide is administered at 600 mg/m$^2$ IV infusion. Each treatment cycle is 21 days, with up to a maximum of 4 cycles of chemotherapy. To begin full-dose chemotherapy on Day 1 of any cycle (Day 22 of the previous cycle), patients must show ANC≥1.5×10$^9$/L and a platelet count≥100×10$^9$/L. In other embodiments, EFLAPEGRASTIM may be administered on Day 2 of each cycle, approximately 24 hours (±2 hours) after TC chemotherapy.

Examples provided here are for illustrative purposes only, and the invention is not intended to be limited by these Examples.

Example 1: Preparation of Complex of Interferon-Alpha (IFNu)-PEG-N-Terminus Region of Immunoglobulin Fc 1-1. Preparation of 1FNa-PEG Conjugate ALD-PEG-ALD (IDB, Korea), which is polyethylene glycol (PEG) having a molecular weight of 3.4 kDa and aldehyde reactive groups at both ends thereof, was added to 5 mg/mL of human interferon alpha-2b (hIFNa-2b, molecular weight: 19 kDa) dissolved in 100 mM phosphate buffer at a molar ratio of hIFNa:PEG of 1:5 to 1:10. A reducing agent, sodium cyanoborohydride (NaCNBH3, Sigma) was added thereto at a final concentration of 20 mM, and allowed to react at 4° C. to 8° C. under slow stirring for about 1 hour. To obtain a conjugate in which PEG is selectively linked to the amino terminus of interferon alpha and PEG and interferon alpha are linked to each other at a ratio of 1:1, the reaction mixture was subjected to SP HP (GE healthcare, USA) anion exchange chromatography to purify an IFNa-PEG conjugate with high purity.

1-2. Preparation of IFNa-PEG-Fc Complex

In order to link the IFNa-PEG conjugate purified in Example 1-1 to the N-terminal proline residue of immunoglobulin Fc, the immunoglobulin Fc fragment was added and reacted at a molar ratio of IFNa-PEG conjugate:immunoglobulin Fc of 1:1 to 1:4. The reaction solution was prepared as 100 mM phosphate buffer (pH 5.5 to 6.5), and sodium cyanoborohydride (NaCNBH3, Sigma) was added as a reducing agent at a final concentration of 20 mM to 50 mM. The reaction was allowed at 4° C. to 8° C. for about 12 hours to 16 hours under slow stirring.

1-3. Isolation and Purification of IFNa-PEG-Fc Complex

In order to remove unreacted materials and by-products after the binding reaction of Example 1-2 and to purify the IFNa-PEG-Fc protein complex thus produced, the reaction mixture was buffer-exchanged to 10 mM Tris (pH 7.5), and then passed through a Source Q (GE healthcare, USA) anion exchange chromatography column to remove unreacted Fc and to obtain an IFNa-PEG-Fc protein complex fraction. In detail, the reaction solution was applied to Source Q column equilibrated with 10 mM Tris (pH 7.5), and the column was subjected to isocratic solvent washing using 20 mM Tris (pH 7.5) buffer solution containing 50 mM sodium chloride (NaCl) to remove impurities. Then, the IFNa-PEG-Fc protein complex was eluted with a concentration gradient of a buffer solution containing 150 mM sodium chloride (NaCl). A small amount of unreacted Fc and interferon alpha dimer were present as impurities in the obtained 1FNa-PEG-Fc protein complex fraction. In order to remove the impurities, Source iso (GE Healthcare, USA) hydrophobic chromatography was further performed. In detail, Source iso (GE Healthcare, USA) was equilibrated with a 20 mM potassium phosphate (pH 6.0) buffer solution containing about 1.3 M ammonium sulfate, and then the purified IFNa-PEG-Fc protein complex fraction was applied thereto. Finally, a high-purity IFNa-PEG-Fc protein complex was purified with a linear concentration gradient of a 20 mM potassium phosphate (pH 6.0) buffer solution. N-terminal selectivity of the Fc region of the prepared IFNa-PEG-Fc protein complex was examined by peptide mapping, and the selectivity was found to be 90% or higher.

Example 2: Preparation of Human Granulocyte Colony-Stimulating Factor (G-CSF)-PEG-Fc Complex The $^{17,65S}$G-CSF-PEG-Fc protein complex was prepared using a derivative ($^{17,65}$-G-CSF) prepared by substituting serine for the amino acids at positions 17 and 65 of the native G-CSF, and then purified.

2-1. Preparation of $^{17,65S}$G-CSF-PEG Conjugate

ALD-PEG-ALD (IDB, Korea), which is polyethylene glycol (PEG) having a molecular weight of 3.4 kDa and aldehyde reactive groups at both ends thereof, was added to 5 mg/mL of $^{17,65}$S-G-CSF (molecular weight: 18 kDa) dissolved in 100 mM phosphate buffer at a molar ratio of G-CSF:PEG of 1:5 to 1:10. A reducing agent, sodium cyanoborohydride (NaCNBH3, Sigma), was added thereto at a final concentration of 20 mM, and allowed to react at 4° C. to 8° C. under slow stirring for about 1 hour. To obtain a conjugate in which PEG is selectively linked to the amino terminus of human granulocyte colony-stimulating factor and PEG and G-CSF are linked to each other at a ratio of 1:1, the reaction mixture was subjected to SP HP (GE Healthcare, USA) cation exchange chromatography to purify a $^{17,65S}$G-CSF-PEG conjugate with a high purity.

2-2. Preparation of $^{17,65}$G-CSF-PEG-Fc Complex

In order to link the $^{17,65}$G-CSF-PEG conjugate purified in Example 3-1 to the N-terminus of immunoglobulin Fc, the immunoglobulin Fc fragment was added and reacted at a molar ratio of 17,65S-G-CSF-PEG conjugate:immunoglobulin Fc of 1:1 to 1:4. The reaction solution was prepared as a 100 mM phosphate buffer (pH 5.5 to 6.5), and sodium cyanoborohydride (NaCNBH3, Sigma) was added as a reducing agent at a final concentration of 20 mM. The reaction was allowed at 4° C. to 8° C. under slow stirring.

2-3. Isolation and Purification of $^{17,65}$G-CSF-PEG-Fc Complex

In order to remove unreacted materials and by-products after the binding reaction of Example 3-2 and to purify the $^{17,65}$G-CSF-PEG-Fc protein complex thus produced, the reaction mixture was buffer-exchanged to 10 mM Tris (pH 8.0) containing 2 M NaCl and then passed through a Source Phenyl column. To remove impurities, the $^{17,65}$S-G-CSF-PEG-Fc protein complex was purified with a concentration gradient of 20 mM Tris (pH 8.0) buffer solution. A small amount of unreacted immunoglobulin Fc and $^{17,65}$G-CSF dimer as impurities were present in the obtained $^{17,65}$G-CSF-PEG-Fc protein complex fraction. In order to remove the impurities, Q HP (GE Healthcare, USA) anion chromatography was further performed. Q HP (GE Healthcare, USA) was equilibrated with a 20 mM Tris (pH 8.0) buffer solution, and then the purified $^{17,65}$G-CSF-PEG-Fc protein complex fraction was applied thereto. Finally, a high-purity $^{17,65}$G-CSF-PEG-Fc protein complex was purified with a linear concentration gradient of a 20 mM Tris (pH 8.0) buffer solution containing 1 M sodium chloride. N-terminal selectivity of the Fc region of the prepared $^{17,65S}$G-CSF-PEG-Fc protein complex was examined by peptide mapping, and the selectivity was found to be 90% or higher.

Example 3: Preparation of Protein Complex Using PEG with Different Reactive Groups 3-1. Preparation of $^{17,65S}$-G-CSF-PEG Conjugate SMB-PEG-SMB (Nektar, USA), which is polyethylene glycol (PEG) having a molecular weight of 3.4 kDa and succinimidyl alpha-methyl butanoate (SMB) reactive groups at both ends thereof, was added to 10 mg/mL of $^{17,65S}$-G-CSF (molecular weight 18 kDa) dissolved in 20 mM phosphate buffer (pH 8.0) at a molar ratio of G-CSF:PEG of 1:3, and allowed to react at room temperature under slow stifling for about 30 minutes. To obtain a conjugate in which PEG is selectively linked to the amino terminus of $^{17,65S}$-G-CSF and PEG and 17,65S-G-CSF are linked to each other at a ratio of 1:1, the reaction mixture was subjected to SP HP (GE Healthcare, USA) cation exchange chromatography.

3-2. Preparation of $^{17,65S}$-G-CSF-PEG-Fc Complex

In order to link the $^{17,65\ S}$-G-CSF-PEG conjugate purified in Example 7-1 to a region other than the N-terminus of immunoglobulin Fc, the immunoglobulin Fc fragment was added and reacted at a molar ratio of $^{17,65}$ $^S$-G-CSF-PEG conjugate:immunoglobulin Fc of 1:4 to 1:8. The reaction was allowed in 20 mM phosphate buffer (pH 5.5 to 6.5) at room temperature for about 2 hours under slow stifling.

3-3. Isolation and Purification of $^{17,65}$ $^S$-G-CSF-PEG-Fc Complex

In order to remove unreacted materials and by-products after the binding reaction of Example 7-2 and to purify the $^{17,65}$ $^S$-G-CSF-PEG-Fc protein complex thus produced, the reaction mixture was passed through a Q HP (GE Healthcare, USA) anion exchange chromatography column and thus unbound Fc was removed and a $^{17,65}$ $^S$-G-CSF-PEG-Fc protein complex fraction was obtained. The reaction solution was applied to a Q HP column equilibrated with 20 mM Tris (pH 8.0) buffer, and the $^{17,65}$ $^S$-G-CSF-PEG-Fc protein complex was purified with a concentration gradient of a buffer solution containing 1 M sodium chloride (NaCl). A small amount of unreacted immunoglobulin Fc and $^{17,65}$ $^S$-G-CSF dimer as impurities was present in the obtained $^{17,65}$ $^S$-G-CSF-PEG-Fc protein complex fraction. In order to remove the impurities, Source iso (GE Healthcare, USA) hydrophobic chromatography was further performed. Finally, a high-purity $^{17,65}$ $^S$-G-CSF-PEG-Fc protein complex was purified with a linear concentration gradient of 50 mM Tris (pH 7.5) buffer solution containing 1.2 M ammonium sulfate using Source iso (GE Healthcare, USA). N-terminal selectivity of the Fc region of the prepared $^{17,65}$ $^S$-G-CSF-PEG-Fc protein complex was examined by peptide mapping, and the selectivity was found to be 90% or higher.

Example 4: Preparation of Protein Complex Using PEG with Different Reactive Groups A FacVII-ATKAVC-PEG-Fc complex was prepared using FacVII-ATKAVC, which is a FacVII derivative of Korean Patent Application No. 10-2012-0111537 previously submitted by the present inventors.

4-1. Isolation and Purification of PEG-Fc Complex

First, to link an aldehyde reactive group of maleimide-10 kDa-PEG-aldehyde (NOF, Japan) to the N-terminus of immunoglobulin Fc fragment, the immunoglobulin Fc region and maleimide-kDa PEG-aldehyde were mixed at a molar ratio of 1:1 in a 100 mM phosphate buffer solution (pH 5.5 to 6.5), and a reducing agent, 20 mM sodium cyanoborohydride (NaCNBH3, Sigma), was added thereto under a protein concentration of 10 mg/mL. The reaction was allowed at a low temperature (4° C. to 8° C.) for about 2 hours. To obtain a monoPEGylated immunoglobulin Fc fragment (maleimide-10 kDa PEG-Fc), Source Q (GE Healthcare, USA) anion chromatography was performed, and elution was performed with a concentration gradient of sodium chloride in 20 mM Tris buffer at pH 7.5.

4-2. Preparation of FacVII-ATKAVC-PEG-Fc Complex

FacVII-ATKAVC was reacted in 10 mM glycylglycine buffer at pH 5.5 at room temperature for about 2 hours by adding 0.5 mM to 2 mM triphenylphosphine-3,3',3"-trisulfonic trisodium salt hydrate as a reducing agent so as to reduce the C-terminus. The C-terminus-reduced FacVII-ATKAVC and monoPEGylated immunoglobulin Fc fragment (maleimide-10 kDa PEG-Fc) were mixed at a molar ratio of 1:4 to 1:20, and the reaction was allowed at a total protein concentration of 1 mg/mL to 2 mg/mL in 50 mM Tris buffer at pH 7.5 at room temperature for about 2 hours.

4-3. Isolation and Purification of FacVII-ATKAVC-PEG-Fc Complex

The reaction solution of Example 8-2 was subjected to Source Q anion chromatography, and the FacVII-ATKAVC-10 kDa PEG-Fc complex was eluted with a concentration gradient of sodium chloride in a 20 mM Tris buffer solution at pH 7.5. To activate FacVII of the FacVII-ATKAVC-PEG-Fc complex, reaction was allowed in a 0.1 M Tris-HCl buffer solution at pH 8.0 under conditions of about 4 mg/mL of FacVII for about 18 hours at a low temperature (4° C. to 8° C.). Finally, high-purity FacVIIa-ATKAVC-PEG-Fc was purified by size exclusion chromatography (GE Healthcare, USA) using Superdex 200 in a 10 mM glycylglycine buffer solution at pH 5.5. N-terminal selectivity of the Fc region of the prepared FacVIIa-ATKAVC-PEG-Fc protein complex was examined by peptide mapping, and the selectivity was found to be 90% or higher.

Example 5: Preparation of Protein Complex Using PEG with a Different Molecular Weight ALD-PEG-ALD (Nektar, USA), which is polyethylene glycol having a molecular weight of 10 kDa and reactive aldehyde groups at both ends thereof, was used to prepare and purify an insulin-10 kDa PEG conjugate in the same manner as in Example 5-2. The purified insulin-10 kDa PEG conjugate was concentrated to a concentration of about 5 mg/mL and then used to prepare and purify an insulin-10 kDa PEG-Fc protein complex in the same manner as in Example 2-3.

Figure 1B:
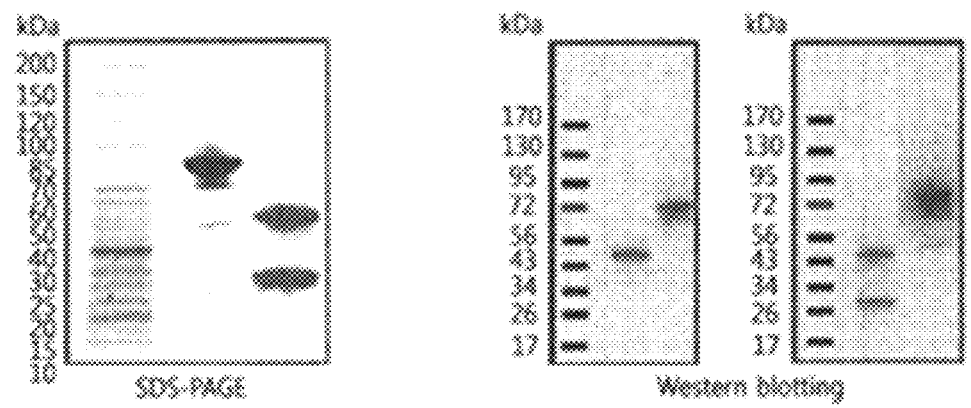
FIG. 1B shows a result of peptide mapping for analyzing Fc region N-terminal binding of a $^{17,65}$Ser-G-CSF-PEG-Fc complex, which was prepared by N-terminal reaction of an immunoglobulin Fc region.

Example 6—Evaluation of Purity of Protein Complex 6-1. Identification of Protein Complex The protein complexes prepared in the above Examples were analyzed by non-reduced SDS-PAGE using a 4% to 20% gradient gel and a 12% gel. SDS-PAGE analysis and Western blot analysis of individual protein complexes using antibodies against immunoglobulin Fc and physiologically active polypeptides were performed. As shown in FIG. 1, a coupling reaction resulted in the successful production of IFNa-PEG-Fc (A), hGH-PEG-Fc (B), $^{17,65S}$G-CSF-PEG-Fc (C), Insulin-PEG-Fc (D), EPO-PEG-Fc (E), CA-Exendin4-PEG-Fc (F), and FacVII-PEG-Fc (G).

6-2. Evaluation of Purity of Protein Complex

The protein complexes prepared in the above Examples, IFNa-PEG-Fc (A), hGH-PEG-Fc (B), $^{17,65S}$G-CSF-PEG-Fc (C), Insulin-PEG-Fc (D), EPO-PEG-Fc (E), and CA-Exendin4-PEG-Fc (F), were subjected to size exclusion chromatography, reverse phase chromatography, or ion exchange chromatography using HPLC, respectively. They displayed a single peak corresponding to high purity of 95% or higher in each analysis.

6-3. Examination of Site Selectivity of the Protein Complex

The protein complexes prepared in Examples, IFNa-PEG-Fc (A), hGH-PEG-Fc (B), $^{17,65S}$G-CSF-PEG-Fc (C), insulin-PEG-Fc (D), and EPO-PEG-Fc (E), were subjected to peptide mapping analysis (reverse phase chromatography) using protease, respectively. It was confirmed that the protein complexes linked via the N-terminus of the immunoglobulin Fc region with high selectivity of 90% or higher were prepared.

Example 7: Comparison of Efficacy of Complex Depending on Fc Binding Position

The protein complexes prepared in Examples, CA-Exendin4-PEG-Fc, $^{17,65}$ $^S$-G-CSF-PEG-Fc, and EPO-PEG-Fc, were subjected to in vitro and in vivo efficacy tests, respectively. As shown in the following Table, binding to the N-terminus (proline) of Fc showed better efficacy than binding to other regions (e.g., lysine).

TABLE 1 in vitro activity - CHO/GLP-1R bioassay of CAExendin-PEG-Fc positional isomers

| Test material | EC50 (ng/ml) | % vs. Experimental group |
|---|---|---|
| CA Exendin (lysine)-PEG-(N-terminus) Fc - Experimental group | 95.35 | 100.00 |
| CA Exendin (lysine)-PEG-(lysine) Fc | 59037 | 16.15 |

As shown in Table 1, comparison of in vitro activities between CA Exendin-PEG-Fc positional isomers showed that the CA Exendin-PEG-Fc complex of the present invention, which was prepared by specific binding to N-terminus of immunoglobulin Fc fragment, has 6 times higher potency than a CA Exendin-PEG-Fc complex which was prepared by binding to another position of an immunoglobulin Fc region.

TABLE 2 in vitro activity - use bone marrow cell proliferation assay of $^{17,65S}$-G-CSF-PEG-Fc positional isomers

| Test material | EC50 (ng/ml) | % vs. Experimental group |
|---|---|---|
| $^{17,65}$S-G-CSF- (N-terminus)-PEG-(N-Terminus) Fc-Experimental Group | 134.43 | 100.00 |
| $^{17,65}$S-G-CSF- (N-terminus)-PEG-(lysine) Fc | 225.87 | 59.50 |

As shown in Table 2, comparison of in vitro activities between $^{17,65S}$-G-CSF-(N-terminus)-PEG-(N-Terminus) Fc-Experimental Group S-G-CSF-PEG-Fc positional isomers showed that the $^{17,65S}$-G-CSF-(N-terminus)-PEG-(N-Terminus) Fc-Experimental Group S-G-CSF-PEG-Fc complex of the present invention, which was prepared by specific binding to a N-terminus of immunoglobulin Fc fragment, has about 67% increased titer, compared to a $^{17,65S}$-G-CSF-(N-terminus)-PEG-(N-Terminus) Fc-Experimental Group S-G-CSF-PEG-Fc complex which was prepared by binding to another position of an immunoglobulin Fc region.

Meanwhile, to examine in vivo activities of the protein complex of the present invention, in particular, EPO-PEG-Fc positional isomers, a normocythemic mice assay was performed to measure reticulocyte levels after subcutaneous injection of EPO-PEG-Fe into normocythemic mice.

TABLE 3

Measurement of in vivo bio-potency reticulocyte level of EPO-PEG-Fc positional isomers (after subcutaneous injection into normocythemic mice).

| Test material | Bio-potency (IU/mg) | % vs. Experimental group |
|---|---|---|
| EPO (N-terminus 84.4%)PEG-(N-Terminus 100%) Fc-Experimental Group | 14,189,403 | 100.00 |
| EPO (N-terminus 38.2%)-PG-(lysine 83.0%) Fc | 225.87 | 59.50 |

As shown in Table 3, comparison of in vivo activities between EPO-PEG-Fc positional isomers showed that the EPO-PEG-Fc complex of the present invention, which was prepared by specific binding to N-terminus of immuno-globulin Fc fragment, has about 40% increased titer, compared to an EPO-PEG-Fc complex which was prepared by binding to another position of an immunoglobulin Fc region.

These results suggest that when the protein complex comprising the physiologically active polypeptide, the non-peptidyl polymer, and the immunoglobulin Fc region is prepared by using a specific site of the immunoglobulin Fc fragment as a binding site, the protein complex shows an improved in vivo activity of the physiologically active polypeptide.

Example 8: Randomized Human Trial $^{17,65S}$G-CSF-PEG-Fc Protein Complex (Eflapegrastim) Vs. Pegfilgrastim in the Management of Chemotherapy-Induced Neutropenia in Breast Cancer Patients Receiving Docetaxel and Cyclophosphamide (TC)

To evaluate the efficacy and safety of a fixed dose of eflapegrastim (13.2 mg/0.6 mL; 3.6 mg GCSF equivalent) in patients with breast cancer who were candidates for adjuvant or neoadjuvant chemotherapy with docetaxel and cyclo-phosphamide (TC), open-label, active-controlled, human studies were conducted in 406 patients.

Eligible patients were randomized 1:1 to the following two treatment arms: (a) eflapegrastim arm:eflapegrastim 13.2 mg/0.6 mL (3.6 mg G-CSF equivalent) fixed dose and (b) pegfilgrastim arm:pegfilgrastim 6 mg/0.6 mL (equivalent to 6.0 mg G-CSF) fixed dose. Accordingly, TC was administered on Day 1 of each cycle intravenously (IV) was: (i) Docetaxel at 75 mg/m$^2$ IV infusion per institute's standard of care (ii) Cyclophosphamide 600 mg/m$^2$ IV infusion per institute's standard of care. Each treatment cycle was 21 days with up to a maximum of 4 cycles of chemotherapy. To begin full-dose chemotherapy on Day 1 of any cycle (Day 22 of the previous cycle), patients must have ANC≥1.5×10$^9$/L and a platelet count≥100×10$^9$/L.

Eflapegrastim or pegfilgrastim were administered on Day 2 of each cycle, approximately 24 hours (±2 hours) after TC chemotherapy. Pegfilgrastim was to be administered according to the manufacturer's Prescribing Information (6 mg subcutaneously once per chemotherapy cycle).

Patients meeting all inclusion and exclusion criteria were randomized to either the eflapegrastim arm or the pegfil-grastim arm and received study treatment (TC) followed 24 (±2) hours by either eflapegrastim or pegfilgrastim for 4 cycles. End of treatment (EOT) visits were performed 35(±5) days from the last dose of study treatment. During Cycle 1, CBC samples were drawn on Day 1 prior to the chemotherapy and then daily from Days 4 to 15 or until recovery from neutropenia. In Cycles 2 to 4, CBC samples were drawn on Day 1 predose and then on Days 4, 7, and 15 (±1 day for each collection). CBC was also collected at the End-of-Treatment Visit. Sparse PK samples for population PK were collected in Cycle 1 on Day 2, Day 4, and Day 5 and then in Cycle 3 on Day 2, Day 4, and Day 7. Immunogenicity samples were drawn at each cycle before chemotherapy administration, at the end of treatment, and at 6 and 12 months (long term safety).

Figure 3:
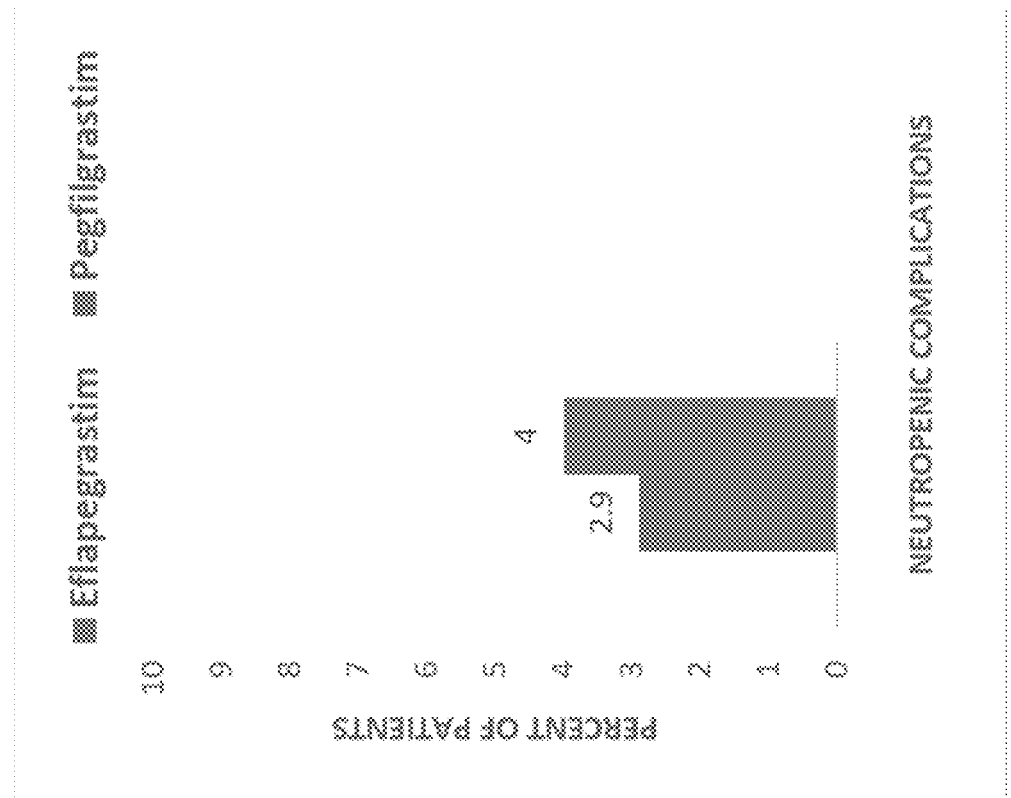
FIG. 3 shows that neutropenic complications, including hospitalizations due to severe neutropenia and/or use of anti-infective for neutropenia, are significantly less in the eflapegrastim arm.
Figure 2:
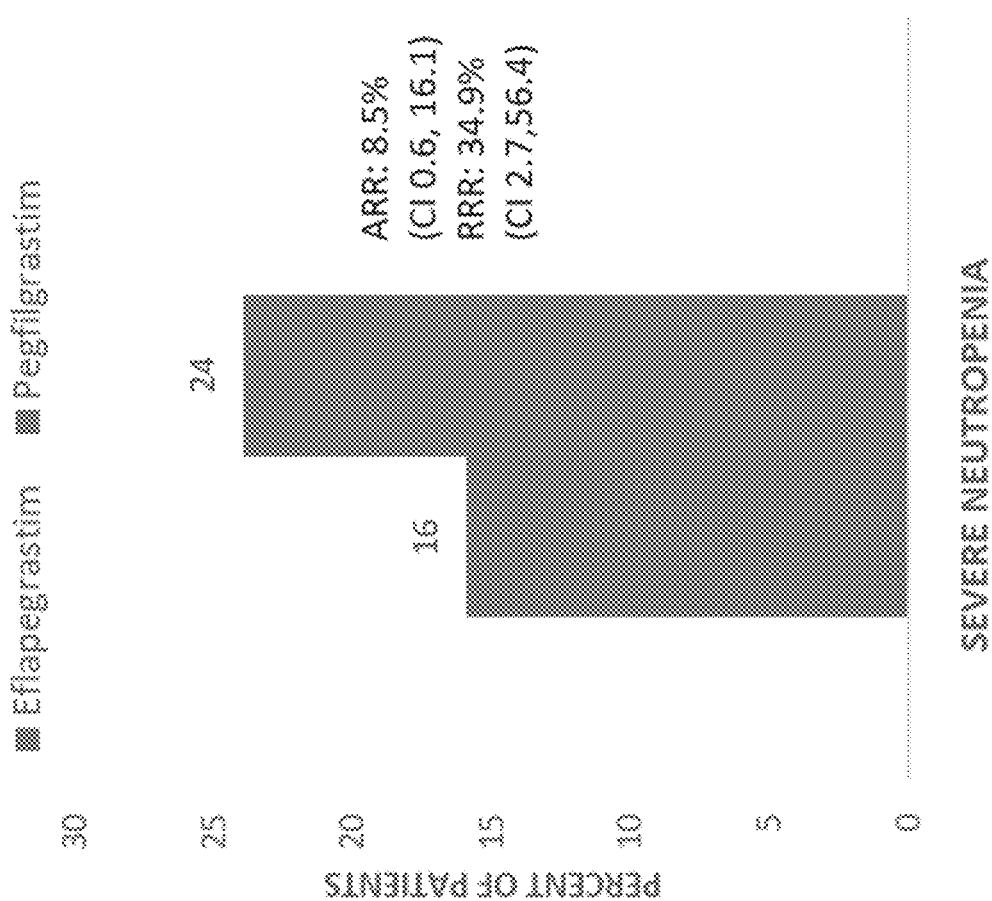
FIG. 2 shows that lower incidence of severe neutropenia in the $^{17,65}$Ser-G-CSF-PEG-Fc (eflapegrastim) arm is statistically significant.

Patients who received at least one dose of study drug and did not discontinue from the study are being followed for long term safety after the last dose of study treatment. The long-term safety includes adverse event (AE) assessment via telephone at 3 months and 9 months and clinic visits for AE assessment and immunogenicity blood draw at 6 months and 12 months. The DSN in Cycle 1 is defined as the number of postdose days of severe neutropenia Efficacy analysis was measured based on the Duration of Severe neutropenia (DSN) in Cycle 1 defined as the number of postdose days of severe neutropenia (ANC<0.5×10$^9$/L) from the first occurrence of an ANC below the threshold. The results showed that the mean DSN for the eflapegrastim arm was 0.20 (±0.50) days compared with a mean DSN of 0.35 (±0.68) days in the pegfilgrastim arm. The difference in mean DSN between the eflapegrastim arm and the pegfilgrastim arm was −0.15 days, and the corresponding 95% CI was (−0.264, −0.032) using the percentile method as specified in the statistical analysis plan. Using the pre-specified criterion for the primary endpoint, the eflapegrastim arm to the pegfilgrastim arm was demonstrated to provide better or as effective as pegfilgrastim (upper bound of 95% CI<0.62 days; p<0.0001). The results demonstrated a statistical superiority of eflapegrastim over pegfilgrastim in cycle 1 (upper bound of 95% CI<0; p=0.038), indicating that the incidence of severe neutropenia is significantly lower in eflapegrastim arm (FIG. 2 and FIG. 3). In the meantime, the incidences of adverse events were substantially were comparable between treatment groups, most of which were considered relating to the chemotherapy (TC) administration.

Example 9: Open-Label Human Trial to Evaluate Duration of Severe Neutropenia after the Same-Day, Varying Dosing Time Schedules of $^{17,65S}$G-CSF-PEG-Fc Protein Complex (Eflapegrastim) Administration in Patients with Breast-Cancer Receiving Docetaxel and Cyclophosphamide To explore the possibility of dosing eflapegrastim on the same day as chemotherapy, and to identify the optimal timing for same-day dosing, an open-label human trial is designed to assess the impact of different doses and dosing times on the duration of neutropenia and on absolute neutrophil counts in chemotherapy-induced neutropenic patients with breast cancer who underwent a treatment course with docetaxel and cyclophosphamide (TC). Current practice is for the patient to return to the clinic approximately 24 hours after TC treatment for a subcutaneous injection of a G-CSF product. However, at least one shortcoming associated with such approach is follow up patient compliance as they may, for example, miss their visits due to adverse events or other complications caused by the TC treatment. The present trial is designed to investigate the use of eflapegrastim when administered the same day as TC at 3 dose time schedules (30 minutes, 3 hours, and 5 hours) after TC administration.

Eligible patients will enter an open-label trial to the following three treatment arms: (a) arm 1: at least 15 patients receive eflapegrastim 13.2 mg/0.6 mL (3.6 mg G-CSF equivalent) administration is 30 minutes±5 minutes, from the end of TC administration (b) Arm 2: at least 15 patients receive eflapegrastim 13.2 mg/0.6 mL (3.6 mg G-CSF equivalent) administration is 3 hours±15 minutes from the end of TC administration (c) Arm 3: at least 15 patients receive eflapegrastim 13.2 mg/0.6 mL (3.6 mg G-CSF equivalent) administration is 5 hours±15 minutes from the end of TC administration. The TC treatment consisted of 3 cycles wherein on Day 1 of each cycle: (i) Docetaxel was administered at 75 mg/m$^2$ IV infusion per institute's standard of care (ii) Cyclophosphamide 600 mg/m$^2$ IV infusion per institute's standard of care. Each treatment cycle was 21 days, with up to 3 cycles of chemotherapy.

Among other criteria, eligible patients must have a new diagnosis of histologically confirmed early-stage breast cancer (ESBC), defined as operable Stage I to Stage IIIA breast cancer and a candidate to receive adjuvant or neoadjuvant TC chemotherapy. Further, they must have adequate hematological, renal, and hepatic function as defined by (a) ANC≥1.5×10$^9$/L, (b) Platelet count≥100×10$^9$/L, (c) Hemoglobin≥10 g/dL, (d) Calculated creatinine clearance>50 mL/min, and (e) Total bilirubin≤1.5 mg/dL and (f)) AST)/serum glutamic-oxaloacetic transaminase (SGOT) and alanine aminotransferase (ALT)/serum glutamic-pyruvic transaminase (SGPT)≤2.5×ULN, and alkaline phosphatase ≤2.0×ULN. Patients with previous exposure to filgrastim, pegfilgrastim, or other G-CSF products in clinical development within 3 months prior to the administration of eflapegrastim were excluded from the study. Blood for CBC and PK analysis will be drawn before TC dose on Day 1 and post eflapegrastim dose at 1, 3, 6, and 8 hours (±15 min), 24, 48, and 72 hours (±2 hours), 144 hours (Day 7±1 day) and 192 hours (Day 9±1).

Even though patients can withdraw for any reasons, they nevertheless must withdraw from the study drug treatment if (a) they develop an adverse event (AE) that interferes with the patient's participation, (b) discontinue the TC regimen, (c) discontinue or deny eflapegrastim doses (d) delay their respective TC administration for >42 days since the last study drug administration, and (e) receive treatment with additional myeloid growth factors.

The dose of eflapegrastim to be administered is a fixed-dose 13.2 mg/0.6 mL containing 3.6 mg G-CSF per cycle. However, in Cycle 1, eflapegrastim is administered on the same day as chemotherapy administration and 24 (±3) hours from the end of TC administration in Cycles 2 to 4.

A complete physical examination, including a description of external signs of the neoplastic disease and co-morbidities, is performed at the Screening Visit, and at the End-of-Treatment Visit. Symptom directed physical examinations are conducted at all other visits. Physical examinations are to be completed by a physician or their designee qualified to perform such examinations.

At every clinic visit, the designated health care provider will inquire about adverse events and intercurrent illnesses since the last visit, which will be graded according to the National Cancer Institute (NCI) Common Terminology Criteria for Adverse Events (CTCAE) Version 5.0 for AE grading, and recorded.

In at least one embodiment, patients receiving eflapegrastim at 30 minutes±5 minutes, 3 hours±15 minutes, and 5 hours±15 minutes from the end of TC administration, at 0.6 mL (3.6 mg G-CSF equivalent) doses exhibit the same or a shorter duration of neutropenia as compared to those that receive eflapegrastim after 24 hour after the end of the TC administration.

The Examples provided herein support the superiority of the G-CSF protein complex attached the immunoglobulin Fc region through a PEG moiety to increase in vivo duration of the physiologically active polypeptide and to increase or maintain in vivo activity (potency) at the same time.

Example 10: Eflapegrastim Enhanced Efficacy Compared to Pegfilgrastim in Neutropenic Rats Supports Potential for Same-Day Dosing A major dose-limiting toxicity of chemotherapy in 43% of patients not given myeloid growth factors is neutropenia, with 24% of these patients having severe neutropenia. In addition, severe febrile neutropenia in 9% of patients not treated with growth factors after chemotherapy. Febrile neutropenia increases the risk of infection, leading to patient hospitalization, morbidity, and mortality and can also lead to chemotherapy dose reductions and drug holidays that can result in significantly reduced chemotherapy efficacy.

G-CSF is known to stimulate the proliferation of bone marrow progenitor cells and enhance neutrophil production in vitro and in vivo. The administration of exogenous G-CSF to patients receiving myelosuppressive chemotherapy increases neutrophil counts and results in resolution of chemotherapy-induced neutropenia. For patients at intermediate or high risk for febrile neutropenia, including those receiving myelosuppressive chemotherapy, clinical practice guidelines recommend prophylactic administration of G-CSF 24 hours after the end of chemotherapy to reduce the degree of neutropenia and FN.

Pegfilgrastim (Neulasta) was the first US FDA-approved long-acting G-CSF, developed by pegylating filgrastim at the N-terminal methionine residue with a 20 kDa polyethylene glycol (PEG) molecule. Currently, the American Society of Clinical Oncology (ASCO) guidelines indicate that pegfilgrastim should be administered 1-3 days after chemotherapy, requiring either an additional office visit or wearing of an auto-injection device, making it inconvenient for patients.

Eflapegrastim (HM10460A, SPI-2012, Rolontis®; Spectrum Pharmaceuticals, Irvine, CA, USA and Hanmi Pharmaceuticals, Seoul, South Korea) is a novel, long-acting recombinant human (rh) G-CSF analog currently in late-stage clinical development. Eflapegrastim differs from the currently approved long-acting G-CSF, pegfilgrastim, due to the conjugation of G-CSF to human IgG4 Fc fragment. The Fc fragment is expressed as a homodimer, and the conjugate has a molecular weight of approximately 72 kDa, since only one of the two polypeptide chains of the Fc fragment is conjugated to a single molecule of G-CSF analog (USAN adoption statement). In addition, the IgG4 Fc fragment imparts neonatal Fc receptor (FcRn)-mediated protection from degradation, increased uptake of eflapegrastim into bone marrow, and improved efficacy.

Concomitant administration of G-CSF with myelosuppressive chemotherapy has the potential to increase patient compliance and improve the therapeutic index. However, the simultaneous administration of exogenous G-CSF and chemotherapy could lead to an increased pool of neutrophil precursors susceptible to destruction by chemotherapy, and may lead to an increased risk of neutropenia, needing further evaluation. The present study was performed to evaluate the feasibility of same day dosing of eflapegrastim compared to pegfilgrastim in rodent models of chemotherapy-induced neutropenia.

10.1 Materials and Methods
10.2 Media and Reagents

Eflapegrastim was provided by Hanmi Pharmaceuticals. Pegfilgrastim was purchased from Amgen, Inc, Thousand Oaks, CA, USA. The doses and concentrations of eflapegrastim and pegfilgrastim were expressed as a standardized dose of G-CSF.

Human serum immunoglobulin G (IgG, I. V. Globulin S) was purchased from Green Cross Corporation, Korea.

RPMI1640 (cat. No.: 22400), IMDM; (cat. No.: 12440), FBS (cat. No.: 10082), penicillin-streptomycin (cat. No.: 15140), HEPES buffer (cat. No. 11344-041), and trypsin-EDTA were purchased from Gibco. EMEM (cat. No.: 30-2003) was from ATCC Media Products, and G418 Sulphate (cat. No. 61-234-RG) was obtained from Cellgro. Sodium pyruvate (cat. No.: P4562) and glutamine (cat. No.: G5792) were procured from Sigma. D-phosphate buffered saline (PBS) (cat. No.: LB 001-02) was purchased from Welgene.

10.3 G-CSF Receptor Binding

Surface plasmon resonance technology and the BIAcore 3000 biosensor (GE healthcare) were employed to measure in vitro binding affinity to the G-CSF receptor. Amine-coupling chemistry was used to immobilize the G-CSF receptor on CM5 biosensor chip. (BR-1006-68, GE healthcare). The CM5 sensor chip surface was activated by injecting a 1:1 mixture of 0.1 mol/L N-hydroxysuccinimide (GE healthcare) and 0.1 mol/L 3-(N,N-dimethylamino)propyl-N-ethylcarbodiamide (GE Healthcare). Chinese hamster ovary (CHO) cell-derived soluble recombinant human G-CSF receptor (R&D Systems, 381-050/CF) was bound to give a surface density of 1291 response units. The chip surface was then blocked with ethanolamine/HCl (GE Healthcare), pH 8.5, and washed with a regeneration solution (50 mmol/L NaCl; 5 mmol/L NaOH). In separate experiments, eflapegrastim (5.5-88 nmol/L) or pegfilgrastim (6.25-100 nmol/L) was injected in HBS-P buffer (10 mmol/L HEPES, pH 7.4; 150 mmol/L NaCl; 0.005% polysorbate 20) at 25° C. with a contact time of 4 min (association phase) and washout with HBS-P buffer for 6 min (dissociation phase). Binding affinity was calculated using the 1:1 Langmuir fitting model for each test material.

10.4 In Vitro Bone Marrow Cell Proliferation Assay

The in vitro biological potency of eflapegrastim and pegfilgrastim was determined by measuring [methyl-$^3$H] thymidine (Amersham, TRA-120-1MCi) incorporation in mouse bone marrow cells obtained from femurs of 4-6 weeks old C57BL/6NCrl mice (Korea Orient Bio Inc., Charles River agency). Non-adherent bone marrow cells were incubated with serial 3-fold dilutions of eflapegrastim or pegfilgrastim in RPMI-1640 media at 37° C., 5% $CO_2$ and 95% RH for 54 hours; [methyl-$^3$H] thymidine (25 μL, 0.25 μCi/well) was added, and incubation continued for an additional 18 hours. The cells were harvested onto a Unifilter-96 GF/C plate with a filter mat using a Uniflter-96 harvester (PerkinElmer) and washed. Scintillation cocktail (PerkinElmer) was then added, and the amount of [methyl-$^3$H] thymidine incorporated was determined using a β-counter. The concentration required for 50% of maximal response ($EC_{50}$), i.e., stimulation of [methyl-$^3$H] thymidine incorporation, was determined by performing 4-parameter logistic regression analysis.

10.5 Fcγ Receptors, FcRn, and C1q Binding Assays

Binding to purified Fcγ receptors, FcRn and C1q (Quidel, A400) was studied by ELISA. For FcγRI binding assay, FcγRI was coated on 96-well microplate, serial dilutions of test materials in assay buffer (phosphate-buffered saline, pH 7.4) were added to the wells and incubated for 90-120 min. at ~25° C. (RT). The plates were then washed with assay buffer containing 0.05% Tween and incubated with HRP-conjugated goat anti-human IgG for 90 min. After washing, color was developed using 3,3',5,5'-tetramethylbenzidine (TMB; BD bioscience) substrate and the absorbance was measured at 450 nm using a microplate reader.

For C1q, FcγRIIB, FcγRIIIA, and FcRn binding assays, serial dilutions of the test materials were added to 96-well microplates coated with C1q, or GST fusion proteins of FcγRIIB or FcγRIIIA, or FcRn αβ2. After incubation and washing, HRP-conjugated anti-C1q antibody was added for C1q binding assay, and rabbit-anti-GST antibody and HRP-conjugated anti-rabbit IgG antibody were sequentially added for FcγRIIB, FcγRIIIA, and FcRn binding assays. The absorbance was measured at 450 nm as described above for FcγRI binding assay.

10.6 Cell-Based Fcγ Receptor Binding Assay

Binding of eflapegrastim to Fcγ receptors was studied using U937 cells (ATCC® CRL-1593.2™). Briefly, the cells were incubated with interferon (IFNγ; R&D Systems) at 37° C., in 95% $O_2$/5% $CO_2$ for 18 hours to increase expression of Fc receptors. The cells were then washed once with D-PBS; for the assay, the cells (100 µL, 1×10$^6$ cells/mL) were incubated with indicated dilutions of the test material at RT for 1 hour, washed thrice with D-PBS and fixed in 1% paraformaldehyde (Cytofix) for 5 min at RT. Fixed cells were washed with the assay solution [D-PBS containing 2% FBS and 100 µg/mL serum IgG (IV Globulin from Green Cross)], incubated for 2 hours at RT with biotinylated anti-G-CSF antibody (IBL Human G-CSF Assay Kit, 27131; 200 washed, and incubated for 1 hour at RT with streptavidin-HRP (Sigma, S2438; 200 µL). The cells were washed, resuspended in 100 µL of the assay solution and transferred to a flat-bottomed 96-well plate. Color was developed using TMB substrate, and absorbance was measured at 450 nm.

10.7 FcRn-Mediated Transcytosis

Membrane permeability and transport of eflapegrastim and pegfilgrastim were compared utilizing Madin-Darby canine kidney (MDCK) (ATCC®, CCL-34) cells overexpressing FcRn.[13] Briefly, MDCK and MDCK-FcRn cells were seeded at 2×10$^5$ cells per well on collagen coated 24 mm Transwell® membrane inserts (Corning, 3491) and cultured for about 48 hours. The conditioned medium of upper and lower wells were replaced with assay medium (Serum free Eagle's minimal essential medium, pH 6.0). Eflapegrastim or pegfilgrastim diluted to 10 µM with the assay medium was loaded into the upper wells and were incubated for 1 hour at 37° C. in 95% $O_2$/5% $CO_2$. The quantity of eflapegrastim and pegfilgrastim transported through the cell layer to the lower wells was determined by ELISA using a human G-CSF ELISA kit (IBL, 27131).

10.8 Efficacy in Chemotherapy-Induced Neutropenia

Two in vivo studies using different chemotherapeutic regimens were used to assess the impact of administration time of eflapegrastim and pegfilgrastim post-chemotherapy in 8-week-old male Sprague-Dawley (SD) rats (Korea Orient bio Inc, Charles River Laboratories). The study designs are depicted in Table 4. In the first study, following current ASCO guidelines for administration of G-CSF post chemotherapy, cyclophosphamide (CPA) was administered intraperitoneally (i.p.) at 50 mg/kg followed by subcutaneous (s.c.) administration of G-CSF 24 hours posttreatment. In the second study, chemotherapy-induced neutropenia was induced using docetaxel (4 mg/kg) and CPA (32 mg/kg) (TC) administered i.p. followed by the administration of G-CSF s.c. concomitant to chemotherapy and at 2, 5, and 24 hours post chemotherapy.

In both studies venous blood samples were collected for determination of absolute neutrophil count (ANC) (Sysmex XN1000-V (Sysmex, Japan) as outlined Table 4 for time to recovery. Total exposure was determined by calculating the area under the ANC-versus-time effect curve above baseline ($AUEC_{ANC}$) for individual animals by subtracting the effects of chemotherapy alone at corresponding times.

10.9 Tissue Distribution in Chemotherapy-Induced Neutropenia

Chemotherapy-induced neutropenia was induced in male SD rats by administering CPA (50 mg/kg, i.p.). Four days later, eflapegrastim (100 µg/kg as G-CSF) or pegfilgrastim (100 µg/kg as G-CSF) was administered s.c. to 15 animals per group. At 8, 30, 54, 72, and 96 hours post G-CSF therapy, three animals per group were euthanized, and serum and bone marrow G-CSF levels were determined via ELISA (IBL Cat. No. JP27131).

10.10 Statistical Analysis

All results are expressed as mean±Standard error of mean (SEM). Statistical analysis consisted of a one-way analysis of variance followed by an unpaired two-tailed t-test and if appropriate, Tukey's multiple comparison test. $P<0.05$ was considered statistically significant. Statistical analysis was performed using Microsoft Excel or GraphPad Prism version 8.3.

10.11 Results 10.12 In Vitro Activity of Eflapegrastim is Similar to that of Pegfilgrastim To determine the affinity of eflapegrastim and pegfilgrastim to the G-CSF receptor, surface plasmon resonance analysis was performed using CHO cell-derived soluble human G-CSF receptor. The equilibrium dissociation constant (KD) values were similar for eflapegrastim (3.6 nM) and pegfilgrastim (2.9 nM).

Since G-CSF is known to induce proliferation of myeloid progenitor cells in bone marrow,[14] the biological activity of eflapegrastim versus pegfilgrastim were examined by measuring their ability to stimulate proliferation of mouse bone marrow-derived cells. The $EC_{50}$ value (expressed as concentration of G-CSF in ng/mL) of eflapegrastim (0.11±0.02) was similar to that of pegfilgrastim (0.13±0.02).

10.13 Eflapegrastim does not Bind to C1q or Fcγ Receptors

Human IgG4 is known to bind to Fcγ receptors (FcγRs).[15] Furthermore, glycan moieties in the Fc fragment are known to interfere with FCγR binding and elicit immune effector functions such as antibody-dependent cell-mediated cytotoxicity (ADCC) and complement-dependent cytotoxicity (CDC).[16] Fc fragment of eflapegrastim, manufactured from recombinant E. coli cells, is aglycosylated and not expected to bind to FcγRs or C1q. Results confirmed that Fc fragment of eflapegrastim and eflapegrastim failed to bind to various FcγRs (FIGS. 4A, 4B, and 4C) or FcγRs expressed in U937 cells (FIG. 4D) or C1q (FIG. 4E).

10.14 Eflapegrastim Binds to FcRn and Undergoes FcRn-Mediated Transcytosis

Figures 5A, 5B:
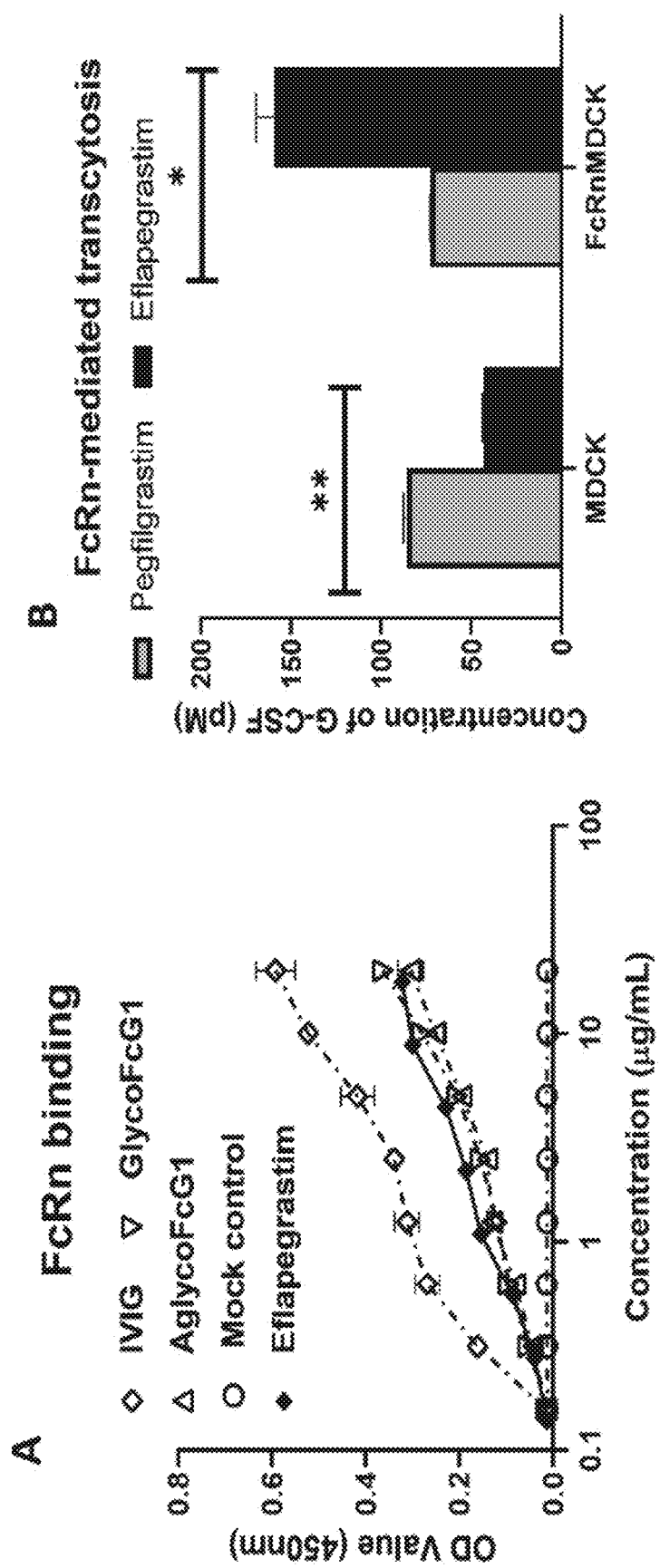
FIGS. 5A and 5B (collectively "FIG. 5") are a set of graphs showing FcRn binding and FcRn mediated Transcytosis. Binding of eflapegrastim to FcRn was studied by ELISA (FIG. 5A). The concentration of individual test articles was calculated based on the theoretical Fc protein to make equivalent molarity. For studying transcytosis (FIG. 5B), the quantity of eflapegrastim and pegfilgrastim transported across the cell layer was determined by ELISA. The data are presented as mean values from duplicate samples. The error bars represent SEM values. *$p<0.05$; **$p<0.01$. OD: optical density. FcRn: neonatal Fc receptor; IVIG: intravenous immunoglobulin G; GlycoFcG1: glycosylated Fc fragment of human IgG1; AglycoFcG1: Aglycosylated Fc fragment of human IgG1; MDCK: Madin-Darby Canine Kidney cells; FcRnMDCK: MDCK cells with over-expressed FcRn obtained by transfection.

The FcRn binds to the Fc domain of IgG and facilitates its transport across endothelial and epithelial barriers.[17,18] Hence it was of interest to determine if eflapegrastim binds to FcRn. Using an ELISA method, eflapegrastim was shown to bind to FcRn with affinities comparable to those of glycosylated and aglycosylated Fc fragments of human IgG1, at levels which are lower than that of serum IgG (FIGS. 5A and 5B).

Transcytosis of eflapegrastim was studied, in comparison with pegfilgrastim using Madin Darby canine kidney (MDCK) cells expressing FcRn on their cell surface. The results presented in FIGS. 5A and 5B show a 4-fold increase in transport of eflapegrastim in FcRn-expressing MDCK cells compared to MDCK-WT cells (43 versus 160 pM); while the transport of pegfilgrastim was similar in FcRn-expressing MDCK and MDCK-WT cells (73 versus 86 pM). These results show that, unlike pegfilgrastim, eflapegrastim can undergo FcRn-mediated transcytosis.

10.15 Eflapegrastim Shows Superior Efficacy in Chemotherapy-Induced Neutropenic Rats The efficacy of eflapegrastim and pegfilgrastim was evaluated in chemotherapy-induced neutropenic rats in two studies. The efficacy of eflapegrastim and pegfilgrastim administered 24 hours after chemotherapy was first evaluated (FIGS. 6A, 6B, and 6C) in accordance with ASCO guidelines.[7] Eflapegrastim doses, expressed as G-CSF equivalent, ranging from 9 to 88 μg/kg were compared with a pegfilgrastim dose of 100 μg/kg (as G-CSF), the pegfilgrastim dose that was found to be effective in stimulating bone marrow cell proliferation in rats.[19] It was subsequently explored the administration of eflapegrastim on the same day as chemotherapy by administering eflapegrastim and pegfilgrastim either concomitantly with chemotherapy, 2 hours, and 5 hours after chemotherapy, or the commonly used time of 24 hours after chemotherapy (FIGS. 7A, 7B, 7C, 7D, 7E, and 7F). In both studies, neutropenic rats did not show any clinical signs during the study period.

Efficacy in Neutropenic Rats Following Administration of Eflapegrastim and Pegfilgrastim 24 Hours after Cyclophosphamide (50 mg/kg) Chemotherapy.

The ANC versus time profiles are shown in FIG. 6A. In the vehicle control, administration of CPA resulted in neutropenia (ANC values below the mean ANC of untreated control group) with a duration of 6-8 days (FIG. 6). Treatment with pegfilgrastim (100 μg/kg as G-CSF) and eflapegrastim (9 to 88 μg/kg as G-CSF) 24 hours after CPA (FIG. 6A) produced an initial increase in ANC above baseline during the first 12 to 24 hours after injection, which then rapidly declined reaching a nadir on Day 2 or 3, increased again reaching a peak on Day 4 or 5 and declined by Day 6 or 7.

The pegfilgrastim treated group as well as different dose groups of eflapegrastim showed statistically significant increases in $AUEC_{ANC}$ (FIG. 6B) and decreases in DN (FIG. 6C) compared to vehicle control. Treatment with eflapegrastim resulted in a dose-dependent increase in $AUEC_{ANC}$ (FIG. 6B) and a decrease in DN (FIG. 6C) as the dose was increased from 9 μg/kg to 53 μg/kg, but there was no further significant increase in $AUEC_{ANC}$ or decrease in DN as the dose was increased to 88 μg/kg (FIGS. 6B and 6C). Treatment with eflapegrastim showed significantly greater increases in $AUEC_{ANC}$ at doses≥53 μg/kg and decreases in DN at doses≥26 μg/kg compared to treatment with pegfilgrastim at 100 μg/kg (FIGS. 6B and 6C). Interestingly, the $AUEC_{ANC}$ and DN in response to the lowest dose level of eflapegrastim (9 μg/kg) were similar to the $AUEC_{ANC}$ and DN in response to 100 μg/kg of pegfilgrastim. These results indicate that eflapegrastim was ~10 fold more potent than pegfilgrastim.

Efficacy in Docetaxel-Cyclophosphamide Induced Neutropenic Rats Following Administration of Eflapegrastim and Pegfilgrastim at 0, 2, 5, and 24 Hours.

FIGS. 7A-D show the ANC profiles following administration of eflapegrastim or pegfilgrastim to rats at 0, 2, 5 and 24 hours after chemotherapy, respectively. In the vehicle control group, administration of docetaxel-cyclophosphamide resulted in neutropenia with a duration of 6-8 days. Treatment with pegfilgrastim or eflapegrastim elicited an initial increase in ANC above baseline during the first 12 to 24 hours post-treatment, then rapidly declined reaching a nadir on Day 3. In eflapegrastim treated neutropenic rats, post-nadir ANC reached a peak on Day 5 or 6 and declined thereafter. In pegfilgrastim treated rats, ANC values at nadir were ~2 fold less than eflapegrastim with post-nadir recovery in ANC markedly reduced through Day 8. Post-nadir increases in ANC were also more pronounced in the eflapegrastim treated group compared to animals treated with pegfilgrastim. Eflapegrastim treated rats showed significantly higher $AUEC_{ANC}$ and lower DN compared to pegfilgrastim treated rats, regardless of time of administration after chemotherapy (FIGS. 7E and 7F).

10.16 Eflapegrastim Reaches Higher Levels in Serum and Bone Marrow in Chemotherapeutic-Induced Neutropenic Rats In view of the superior efficacy of eflapegrastim compared with pegfilgrastim in a neutropenic rat model, the distribution of eflapegrastim into the bone marrow of neutropenic rats was compared with pegfilgrastim. Concentrations of eflapegrastim and pegfilgrastim in serum and in bone marrow were determined at different times following s.c. administration of the test article (Table 5). Eflapegrastim and pegfilgrastim reached peak concentrations in serum and bone marrow at 30 hours after s.c. administration. Eflapegrastim exhibited approximately 3-fold higher exposure ($AUC_{last}$) and peak concentration ($C_{max}$) than pegfilgrastim at similar doses ($AUC_{last}$ 12401 vs 4263 ng·hr/ml; $C_{max}$ 308 versus 125 ng/ml, respectively). The terminal half-lives for both compounds were comparable at approximately 4 hours. The absolute concentrations of eflapegrastim in bone marrow were higher than those of pegfilgrastim at all corresponding time points, and the differences were statistically significant in bone marrow at 30 and 54 hours. Eflapegrastim concentrations also declined at a slower rate than pegfilgrastim in the bone marrow.

10.17 Discussion

Long-acting G-CSFs administered once per chemotherapy cycle offer increased convenience to patients and caregivers' over short-acting G-CSF, which must be administered daily for up to 2 weeks following myelosuppressive chemotherapy treatment. Eflapegrastim is a novel long-acting G-CSF with unique structural features compared to currently approved long-acting pegylated G-CSF products. Eflapegrastim contains an aglycosylated IgG4-Fc fragment conjugated to a human recombinant G-CSF analog via a short PEG linker. The strategy behind this structural modification to G-CSF is to increase the half-life and the ability to penetrate to the site of action without adversely altering affinity or potency. Binding studies with G-CSF receptors demonstrated that eflapegrastim and pegfilgrastim have comparable affinities.

Chemotherapy may cause myelosuppression, potentially reducing bone marrow stem cell proliferation and subsequently decreased ANC. G-CSF treatment improves bone marrow proliferation, myeloid progenitor cell activation, and neutrophil differentiation and migration. Both eflapegrastim and pegfilgrastim displayed similar binding affinity in vitro, suggesting that the addition of the Fc fragment or PEG linker did not perturb G-CSF binding. Although the Fc fusion protein in eflapegrastim has the potential to trigger ADCC by interaction of the Fc fragment with Fcγ receptors on NK cells or neutrophils, no binding of eflapegrastim to Fcγ receptors was observed (FIG. 3) suggesting that eflapegrastim does not exert ADCC.

The neonatal Fc receptor for IgG (FcRn) binds to the Fc portion of IgG and contributes to effective IgG recycling and transcytosis, thereby enhancing tissue residence. FcRn is highly expressed on bone marrow-derived cells and myeloid-derived antigen-presenting cells. Eflapegrastim showed strong binding to FcRn (FIG. 5A) and FcRn dependent transcytosis (FIG. 5B) suggesting, enhanced uptake and retention of eflapegrastim as compared to pegfilgrastim in the bone marrow. (Table 5).

Theoretically, same-day administration of exogenous G-CSF with chemotherapy could lead to an increased pool of neutrophil precursors susceptible to destruction by chemotherapy, which paradoxically may lead to an increased risk of neutropenia. In a retrospective study, Weycker et al. analyzed 45,592 patients who received pegfilgrastim. They reported that the incidence of neutropenia was significantly higher in patients who received pegfilgrastim on the same day as chemotherapy completion compared to those who received it at least 24 hours after the completion of chemotherapy. Burris et al. reviewed three randomized double-blind studies comparing same-day and next-day dosing of pegfilgrastim; there was a statistically insignificant trend toward longer duration of severe neutropenia after same-day dosing with pegfilgrastim compared to next-day dosing.

Eflapegrastim showed strong FcRn binding ability resulting in increased uptake and longer duration of residence in the bone marrow, compared to pegfilgrastim. It was therefore hypothesized that same-day dosing of eflapegrastim might overcome the loss of pegfilgrastim effectiveness. To test this hypothesis, two studies were performed in chemotherapy-induced neutropenic rats. In the first study, eflapegrastim and pegfilgrastim were administered 24-hours post-chemotherapy with CPA as per ASCO guidelines. Eflapegrastim elicited a dose-dependent blunting of the chemotherapy-induced neutropenia with a reduction in the neutrophil nadir and an increased rate of neutrophil recovery (FIG. 6). Pegfilgrastim was also effective in this dose regimen; however, the magnitude of the response was less than that of eflapegrastim. It was observed that when eflapegrastim was administered concomitantly with chemotherapy or up to 5 hours post-chemotherapy, there was a more profound reduction in the degree of neutropenia and a more rapid rate of recovery of ANC compared to pegfilgrastim. When either eflapegrastim or pegfilgrastim was administered the day after chemotherapy with CPA and docetaxel (FIG. 7), similar effects were observed as with CPA alone (FIG. 6). Based on the results of these studies, the bone marrow uptake and retention of both eflapegrastim and pegfilgrastim in neutropenic rats were evaluated. As expected, due to the presence of the Fc fragment, eflapegrastim retention and exposure in bone marrow, as well as in serum, were greater than those of pegfilgrastim. These results provide support for the in vivo findings observed with same day dosing. These results provide support for the in vivo findings observed with same day dosing. Same-day dosing in patients is believed to be less effective because of the associated strength and duration of the initial stimulation of myeloid progenitor cells by G-CSF, rendering these cells more sensitive to the effects of cytotoxic chemotherapy. However, the increased FcRn mediated transcytosis of eflapegrastim may have enhanced its bioavailability when the myeloid progenitors were regenerated, post-chemotherapy.

Therefore, there is the potential for eflapegrastim to be effective when dosed to patients the same day as chemotherapy.

In summary, although eflapegrastim and pegfilgrastim have similar in vitro binding affinity. The FcRn fragment in eflapegrastim increases the uptake of the drug into bone marrow resulting in increased potency in chemotherapy-induced neutropenia. In addition, the greater bone marrow exposure and retention to eflapegrastim resulted in a decrease in the duration of neutropenia when compared to pegfilgrastim. The findings of the present study support further studies in humans with the concomitant administration of eflapegrastim and administration during the first 24 hours of chemotherapy.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds, are therefore intended to be embraced by the claims.

TABLE 4

Study designs chemotherapy-induced neutropenia

| | Study 1 | Study 2 |
|---|---|---|
| Strain | Sprague-Dawley | Sprague-Dawley |
| Number of Animals | 5/group | 5/group |
| Chemotherapy | CPA (50 mg/kg) i.p. | Docetaxel (4 mg/kg) i.p. CPA (32 mg/kg) i.p. |
| Eflapegrastim Doses (as G-CSF) | 9, 26, 53 and 88 µg/kg s.c. | 62 µg/kg s.c. |
| Pegfilgrastim Doses (as G-CSF) | 100 µg/kg s.c. | 100 µg/kg s.c. |
| Control Groups | Nontreatment Control (no CPA) Vehicle Control (DPBS) | Nontreatment Control (no docetaxel/CPA) Vehicle Control (DPBS) |
| Time of G-CSF dose post-chemotherapy | 24 hours | 0 (concomitant), 2, 5, and 24 hours |
| Time of Blood Draws | −1, 0.4, 1, 2, 3, 4, 5, 6, 7, and 8 days | 0 (predose), 0.25, 1, 2, 3, 4, 5, 6, 7, and 8 days |

CPA: cyclophosphamide, DPBS: Dulbecco's phosphate-buffered saline; G-CSF: Granulocyte-colony stimulating factor; i.p: intraperitoneal, s.c: subcutaneous.

TABLE 5

Serum and bone marrow concentrations of eflapegrastim and pegfilgrastim in neutropenic rats following subcutaneous injection

| Time Post-Injection | 8 hours | 30 hours | 54 hours | 72 hours | 96 hours |
|---|---|---|---|---|---|
| Serum (ng/ml as G-CSF) | | | | | |
| Eflapegrastim (100 µg/kg) | 138.8 ± 12.3 | 307.7 ± 17.1* | 179.7 ± 32.2* | 13.2 ± 1.7* | 0.2 ± 0.0 |
| Pegfilgrastim (100 µg/kg) | 120.9 ± 13.2 | 125.2 ± 16.8 | 8.1 ± 1.5 | 0.4 ± 0.037 | 0.1 ± 0.1 |
| Bone Marrow (ng/g as G-CSF) | | | | | |
| Eflapegrastim (100 µg/kg) | 64.4 ± 3.9* | 92.6 ± 2.1* | 62.4 ± 18.3* | 14.7 ± 2.4 | 1.5 ± 0.2 |

TABLE 5-continued

Serum and bone marrow concentrations of eflapegrastim and pegfilgrastim in neutropenic rats following subcutaneous injection

| Time Post-Injection | 8 hours | 30 hours | 54 hours | 72 hours | 96 hours |
|---|---|---|---|---|---|
| Pegfilgrastim (100 μg/kg) | 45.7 ± 4.1 | 44.3 ± 7.7 | 1.9 ± 0.6 | BQL | BQL |

BQL: Below quantification limit;
G-CSF: granulocyte colony-stimulating factor;
NC: Not calculated
Data presented are mean ± SEM values from 3 animals;
*$P < 0.05$ (unpaired T test DF N-1; 2 tailed probability)

What is claimed is:

1. A method of increasing stem cell production in a subject in need thereof, the method comprising administering to the subject a therapeutically effective amount of a chemotherapeutic regimen followed by a therapeutically effective amount of a protein complex comprising a modified human granulocyte-colony stimulating factor (hG-CSF) covalently linked to an immunoglobulin Fc region via a non-peptidyl polymer, wherein the non-peptidyl polymer is site-specifically linked to an N-terminus of the immunoglobulin Fc region and the modified hG-CSF comprises the amino acid sequence of SEQ ID NO: 1.

2. The method of claim 1, wherein the protein complex is administered on the same day as a chemotherapeutic regimen.

3. The method of claim 2, wherein the protein complex is administered to the patient within 30 minutes, 2 hours, 3 hours, 5 hours, 8 hours, or 12 hours of completion of the chemotherapeutic regimen.

4. The method of claim 1, wherein the protein complex is administered between 1 and 5 days after the subject is treated with adjuvant or neoadjuvant chemotherapy.

5. The method of claim 4, wherein the adjuvant or neoadjuvant chemotherapy is a combination of docetaxel and cyclophosphamide.

6. The method of claim 1, wherein the subject has breast cancer.

7. The method of claim 1, wherein a second dose of the protein complex is administered between 15 and 25 days after a first dose of the protein complex is administered to the subject.

8. The method of claim 1, wherein the therapeutically effective amount is a unit dosage between about 5 μg/kg and about 200 μg/kg.

9. The method of claim 1, wherein the therapeutically effective amount is 13.2 mg of the protein complex in a 0.6 mL dosage volume.

10. The method of claim 1, wherein the immunoglobulin Fc region comprises a polypeptide sequence of SEQ ID NO: 2.

11. The method of claim 1, wherein:
(a) the immunoglobulin Fc region is aglycosylated;
(b) the immunoglobulin Fc region consists of one to four domains selected from the group consisting of CH1, CH2, CH3, and CH4 domains;
(c) the immunoglobulin Fc region further comprises a hinge region; or
(d) the immunoglobulin Fc region is an immunoglobulin Fc fragment derived from IgG, IgA, IgD, IgE, or IgM.

12. The method of claim 1, wherein:
(a) each domain of the immunoglobulin Fc fragment is a hybrid of domains, in which each domain has a different origin derived from immunoglobulins selected from the group consisting of IgG, IgA, IgD, IgE, and IgM;
(b) the immunoglobulin Fc fragment is a dimer or multimer consisting of single chain immunoglobulins comprising domains having the same origin;
(c) the immunoglobulin Fc fragment is an IgG4 Fc fragment; or
(d) the immunoglobulin Fc fragment is a human aglycosylated IgG4 Fc fragment.

13. The method of claim 1, wherein the non-peptidyl polymer is selected from the group consisting of polyethylene glycol, polypropylene glycol, an ethylene glycol-propylene glycol copolymer, polyoxyethylated polyol, polyvinyl alcohol, polysaccharide, dextran, polyvinyl ethyl ether, a biodegradable polymer, a lipid polymer, chitin, hyaluronic acid, and a combination thereof.

14. The method of claim 1, wherein the non-peptidyl polymer is polyethylene glycol.

15. The method of claim 14, wherein the polyethylene glycol has a molecular weight of 3.4 kDa.

* * * * *

SEQUENCE LISTING

```
Sequence total quantity: 2
SEQ ID NO: 1              moltype = AA   length = 174
FEATURE                   Location/Qualifiers
source                    1..174
                          mol_type = protein
                          organism = synthetic construct
SEQUENCE: 1
TPLGPASSLP QSFLLKSLEQ VRKIQGDGAA LQEKLCATYK LCHPEELVLL GHSLGIPWAP    60
LSSCSSQALQ LAGCLSQLHS GLFLYQGLLQ ALEGISPELG PTLDTLQLDV ADFATTIWQQ   120
MEELGMAPAL QPTQGAMPAF ASAFQRRAGG VLVASHLQSF LEVSYRVLRH LAQP         174

SEQ ID NO: 2              moltype = AA   length = 221
FEATURE                   Location/Qualifiers
source                    1..221
                          mol_type = protein
                          organism = synthetic construct
SEQUENCE: 2
PSCPAPEFLG GPSVFLFPPK PKDTLMISRT PEVTCVVVDV SQEDPEVQFN WYVDGVEVHN    60
AKTKPREEQF NSTYRVVSVL TVLHQDWLNG KEYKCKVSNK GLPSSIEKTI SKAKGQPREP   120
QVYTLPPSQE EMTKNQVSLT CLVKGFYPSD IAVEWESNGQ PENNYKTTPP VLDSDGSFFL   180
YSRLTVDKSR WQEGNVFSCS VMHEALHNHY TQKSLSLSLG K                       221
```